United States Patent
Higuchi et al.

(10) Patent No.: US 7,108,851 B2
(45) Date of Patent: Sep. 19, 2006

(54) PREVENTION AND TREATMENT OF MYCOPLASMA-ASSOCIATED DISEASES

(76) Inventors: Maria De Lourdes Higuchi, Rua Capote Valente, 361-ApTo, Sao Paulo (BR) 05409001; Sergio Schenkman, Rua Botucatu 862, Sao Paulo (BR) 05023063

( * ) Notice: Subject to any disclaimer, the term of this patent is extended or adjusted under 35 U.S.C. 154(b) by 130 days.

(21) Appl. No.: 10/086,913

(22) Filed: Mar. 1, 2002

(65) Prior Publication Data

US 2003/0124109 A1    Jul. 3, 2003

Related U.S. Application Data

(63) Continuation of application No. PCT/BR01/00083, filed on Jul. 3, 2001.

(51) Int. Cl.
*A61K 38/47* (2006.01)
*A61K 41/00* (2006.01)
(52) U.S. Cl. .................. 424/94.61; 514/789.5
(58) Field of Classification Search ............ 424/94.61; 435/189, 200, 201, 320.1, 325, 6; 530/350; 514/789.5
See application file for complete search history.

(56) References Cited

U.S. PATENT DOCUMENTS 6,281,199 B1    8/2001    Gupta

OTHER PUBLICATIONS

Tsai et al., PNAS USA, 92(22), 10197-201, 1995.*
Umezawa et al., "Enzyme-linked immunosorbent assay with *Trypanosoma cruzi* excreted-secreted antigens (TESA-ELISA) for serodiagnosis of acute and chronic Chagas' disease," *Diagn. Microbiol. Infect. Dis.* 39:169-176, 2001 (USA).
Higuchi et al., "Great amount of *C. pneumoniae* in ruptured plaque vessel segments at autopsy. A comparative study of stable plaques," *Ara. Bras. Cardiol.* 74:149-151(2000).
Higuchi et al., "Detection of *Mycoplasma pneumoniae* and *Chlamydia pneumoniae* in ruptured atherosclerotic plaques," *Braz. J. Med. Biol. Res.* 33:1023-1026 (2000).
Horne et al., "IgA sero-positivity to *Mycoplasma pneumoniae* predicts the diagnosis of coronary artery disease," *J. Am. Coll. Cardiol.* 35:321 (abstract) (2000).
Laroy et al., "Cloning of *Trypanosoma cruzi* trans-Sialidase and Expression in *Pichia pastoris,*" *Protein Expr. Purif.* 20:389-393 (2000).
Buscaglia et al., "Tandem amino acid repeats from *Trypanosoma cruzi* shed antigens increase the half-life of proteins in blood", Blood, 93:2025-2032, (1999).

Cole, "Mycoplasma-induced arthritis in animals: relevance to understanding the etiologies of the human rheumatic diseases," *Rev. Rhum. Engl. Ed.* 66 (1 Suppl):45S-49S (1999).
Berbec et al., "Total serum sialic acid concentration as a supporting marker of malignancy in ovarian neoplasia," *Eur J Gynaecol On col* 20(5-6): 389-392 (1999).
Feng Shaw-Huey, et al., "Mycoplasma infections prevent apoptosis and induce malignant transformation o interleuckin-3-dependent 32D hematopoietic cells," *Mol Cel Biol* 19(12): 7995-8002 (1999).
Nicolson et al., "Mycoplasmal infections in chronic illnesses," (http://www.gulfwarvets.com/article24.htm) also published in *Medical Sentinel*, 4:172-175,191 (1999).
Ros-Bullon , et al., "Serum sialic acid in malignant melanoma patients: na ROC curve analysis," *Anticancer Res* 19(4C): 3619-3622 (1999).
Fu et al., "Middle cerebral artery occlusion after recent *Mycoplasma pneumoniae* infection," *J. Neurol. Sci.* 157:113-115 (1998).
Neyrolles et al., "Identification of two glycosylated components of *Mycoplasma penetrans*:a surface-exposed capsular polysaccharide and a glycolipid fraction," *Microbiology*, 144:1247-1255 (1998).
Razin et al., "Molecular biology and pathogenicity of mycoplasmas," *Microbiol. Mol. Biol. Rev.* 62(4):1094-1156 (1998).
Taylor-Robinson and Thomas, "*Chlamydia pneumoniae* in arteries: the facts, their interpretation, and future studies," *J. Clin. Pathol.* 51:793-797 (1998).
Agusti et al., "The trans-sialidase of *Trypanosome cruzi* is anchored by two different lipids," *Glycobiology* 7(6):731-735 (1997).
Cole, "Mycoplasma interactions with the immune system: implications for disease pathology," 1997, http://www.compkarori.com/arthritis/pil6002.htm).
Danesch et al., Chronic infecFarraj et al., "Mycoplasma-associated pericarditis, case report," *Mayo Clin. Proc.* 72:33-36 (1997).
Farraj et al., "Mycoplasma-associated pericarditis, case report," *Mayo Clin. Proc.* 72:33-36 (1997).
Gurfinkel et al., "IgG antibodies to chlamydial and mycoplasma infection plus C-reactive protein related to poor outcome in unstable angina," *Arch. Inst. Cardiol. Mex.* 67:462-468 (1997).
Ribeirão et al., "Temperature differences for trans-glycosylation and hydrolysis reaction reveal an acceptor binding site in the catalytic mechanism of *Trypanosoma cruzi* trans-sialidase," *Glycobiology* 7:1237-1246 (1997).tions and coronary artery disease: is there a link?, *Lancet* 350:430-436 (1997).

(Continued)

*Primary Examiner*—Maryam Monshipouri
(74) *Attorney, Agent, or Firm*—Baker Botts LLP

(57) ABSTRACT

The present invention relates to the prevention and treatment of diseases associated with undesirable cell proliferation, including atherosclerotic narrowing of blood vessels and malignancy, comprising preventing or treating infection by mycoplasma. It is based, at least in part, on the discovery that, in many cases, mycoplasma infection exists coincident with undesirable cell proliferation and/or proliferation of other infectious organisms.

5 Claims, 16 Drawing Sheets

OTHER PUBLICATIONS

Perez et al., "Leukocytoclastic vasculitis and polyarthritis associated with *Mycoplasma pneumoniae* infection," *Clin. Infect. Dis.* 25:154-155 (1997).
*Trypanosoma cruzi* trans-silaidase, Accession No. BAA09334, GI:840708,1060 aa, Smith et al. (1996).
*Trypanosoma cruzi* trans-silaidase, Accession No. BAA09333, GI:84706, 964 aa, Smith et al. (1996).
Buschiazzo et al., "Medium scale production and purification to homogeneity of a recombinant trans-sialidiase from *Trypanosoma cruzi,*" *Cell Mol. Biol.* 42:703-710 (1996).
Cremona et al., "Effect of primary structure modifications in*Trypanosoma cruzi* neuramindase trans-sialidase activities," *Cell. Mol. Biol.* 42:697-702 (1996).
Umezawa et al., "Immunoblot assay using excreted/secreted antigens of *Trypanosoma cruzi* in serodiagnosis of congenital, acute and chronic Chagas' disease," *J. Clin. Microbiol.* 34: 2143-2147, (1996).
*Trypanosoma cruzi* TCTS-154 gene for trans-sialidase, Accession No. D50684, GI:840705, 2895 bp, Uemura et al. (1995).
*Trypanosoma cruzi* TCTS-121 gene for trans-sialidase, Accession No. D50685, GI:840707, 3183 bp, Uemura et al. (1995).
Cremona et al., "A single tyrosine differentiates active and inactive *Trypanosome cruzi* trans-sialidase," *Gene* 160:123-128 (1995).
Blanchard et al., "AIDS-associated mycoplasmas," *Annu. Rev. Microbiol.* 48:687-712 (1994).
Campetella et al., "A recombinant *Trypanosoma cruzi* trans-sialidase lacking the amino acid repeats retains the enzymatic activity," *Mol. Biochem. Parasitol.* 64:337-340 (1994).
Schenkman et al., "Structural and functional properties of *Trypanosome* trans-sialidase," *Annu. Rev. Microbiol.* 48:499-523 (1994).
Schenkman et al., "A proteolytic fragment of *Trypanosoma cruzi* trans-sialidase lacking the carboxy-terminal domain is active, monomeric, and generates antibodies that inhibit enzymatic activity" *J. Biol. Chem.* 269:7970-7975 (1994).
*Trypanosoma cruzi* trans-sialidase homologue, Accession No. AAC98544, GI:624626, 736 aa, Briones et al.., (1993).
Scudder et al., "Enzymatic characterization of beta-D-galactoside alpha 2,3-trans-sialidase from *Trypanosome cruzi,*" *J. Biol. Chem.* 268(13):9886-9891 (1993).
*Trypanosoma cruzi* trans-sialidase-neuraminidase, Accession No. S28409, GI:323067, 200 aa, Uemura et al., (1992).
Parodi et al., "Identification of the gene(s) coding for the trans-sialidase of *Trypanosome cruzi*" *EMBO J.* 11:1705-1710 (1992).
Schenkman et al., "*Trypanosoma cruzi* trans-sialidase and neuraminidase activities can be mediated by the same enzymes," *J Exp Med* 175(2):567-575 (1992).
Uemura et al., "Only some members of a gene family in *Trypanosome cruzi* encode proteins that express both trans-sialidase and neuraminidase activities," *EMBO J.* 11:3837-3844 (1992).
Vandekerckhove et al., "Substrate specificity of the *Trypanosoma cruzi* trans-sialidase," *Glycobiology* 2(6):541-548, (1992).
Pereira et al., "The *Trypanosoma cruzi* neuraminidase contains sequences similiar to bacterial neuraminidases, YWTD repeats of the low density lipoprotein receptor, and Type III modules of fibronection," *J. Ex. Med.* 174:179-191 (1991).
Pollevick et al., "The complete sequence of a shed acute-phase antigen of *Trpanosoma cruzi,*" *Mol. Biochem. Parasitol.* 47:247-250 (1991).
Schenkman et al., "Attachment of *Trypanosoma cruzi* trypomastigotes to receptors at restricted cell surface domains," *Exp. Parasitol.* 72:76-86 (1991).
Roberts et al., "Sialic Acid-dependent Adhesion of *Mycoplasma pneumoniae* to Purified Glycoproteins," *Journal of Biological Chemistry*, 264:9289-9293 (1989).
Chen et al., "Carditis associated with *Mycoplasma pneumoniae* infection," *Am. J. Dis. Child.* 140:471-472 (1986).
Pereira, "A developmentally regulated neuraminidase activity in *Trypanosoma cruzi,*" *Science* 219:1444-1446 (1983).
Kahane, "Purification of attachment moiety: a review," *Yale J. Biol. Med.* 53:665-669 (1983).

Baseman et al., "Sialic acid residues mediate *Mycoplasma pneumoniae* attachment to human and sheep erythrocytes," *Infect. Immun.* 38(1):389-391 (1982).
Bredt et al., "Adherence of mycoplasmas: phenomena and possible role in the pathogenesis of disease," *Infection* 10(3):199-201 (1982).
Chandler et al., "*Mycoplasma pneumoniae* attachment: competitive inhibition by mycoplasmal binding component and by sialic acid-containing glycoconjugates," *Infect. Immun.* 38(2):598-603 (1982).
Krause et al., "Identification of *Mycoplasma pneumoniae* proteins associated with hemadsorption and virulence," *Infect. Immun.* 35:809-817 (1982).
Hansen et al., "Characterization of hemadsorption-negative mutants of *Mycoplasma pneumoniae,"* *Infect. Immun.* 32:127-136 (1981).
Kahane et al., "Attachment of mycoplasmas to erythrocytes: a model to study mycoplasma attachment to the epithelium of the host respiratory tract," *Isr. J. Med. Sci.* 17:589-592 (1981).
Taylor-Robinson et al., "Mycoplasmal adherence with particular reference to the pathogenicity of *Mycoplasma pulmonis,"* *Isr. J. Med. Sci.* 17:599-603 (1981).
Glasgow and Hill, "Interactions of *Mycoplasma gallisepticum* with sialyl glycoproteins," *Infect. Immun.* 30:353-361 (1980).
Gabridge and Taylor-Robinson, "Interaction of *Mycoplasma pneumoniae* with human lung fibroblasts: rol of receptor sites," *Infect. Immun.* 25:455-459 (1979).
Clyde et al., "Tropism for *Mycoplasma gallisepticum* for arterial walls," *Proc. Natl. Acad. Sci. U.S.A.* 70: 1545-1549 (1973).
Collier and Clyde, "Relationships between *M. pneumoniae* and human respiratory epithelium," *Infect. Immun.* 3:694-701 (1971).
Sachse et al., 1996, "Mechanisms and factors involved in *Mycoplasma bovis* adhesion to cells," Int. J. of Med. Microbiology 284:80-92.
Izumikawa et al., 1986, "*Mycoplasma pneumoniae* attachment to glutaraldehyde-treated human WiDr cell cultures" Proc. Soc. Exp. Biol. Med.
Maida, 1983, "Immunological reactions against *Mycoplasma pneumoniae* in multiple sclerosis: preliminary findings," J. Neurol. 229(2):103-111.
Val'kovich, 1980, "Viral and mycoplasma-induced glomerulopathies in children," Arkh. Pathol. 42(3):10-15.
"A Side effect of neuraminidase inhibitor in a patient with liver cirrhosis" by Kaji, et al. *J. Infect, Chemother*, (2005)(11:41-43).
"Structural Insights into the catalytic mechanism of Trypanosoma cruzi trans-sialidase" by Amaya, et al., *Structure*, vol. 12, pp. 775-784, May 2004.
"Trypanosoma cruzi trans-sialidase as a new therapeutc tool in the treatment of chronic inflammatory diseases: possible action against mycoplasma and chlamydia" by Higuchi, Medical Hypotheses (2004)(63, 616-623).
"Coinfection with mycoplasma pneumoniae and chlamydia pneumoniae in ruptured plaques associated with acute myocardia infarction" by Higuchi, et al., Arq. Bras Cardiol, vol. 81, No. 1, 12-22, 2003.
"Pathophysiology of the heart in chagas'disease: current status and new developments" by Higuchi, et al., 2003 European Society of Cardiology, pp. 96-107.
"Trypanosoma cruzi trans-sialidase operates through a covalent sialyl-enzyme intermediate: Tryosine is the catalytic nucleophile" by Watts, et al., J. Am. Chem. Soc. 2003, 125, 7532-7533.
A possible role for complement in the pathogenesis of chronic chagasic cardiomyopathy by Aiello, et al., Journal of Pathology, 2002, 197;224-229.
The Crystal Structure and Mode of Action of trans-sialidase, a key enzyme in trypanosoma cruzi pathogenesis by Bushiazzo, et al., Molecular Cell, vol. 10, 757-758, Oct. 2002.
Intracellular DNA replication and long term survival of pathogenic mycoplasmas by Dallo, et al., Microbial Pathogenesis, 2000, 29:301-309.

Systematic mapping of hearts from chronic chagasic patients: the association between the occurrence of histopathological lesions and Trypanosoma cruzi antigens by Palomino, et al., Annals of Tropical Medicine and Parasitology, vol. 94, No. 6, 571-579 (2000).

Efficacy and Safety of the Oral Neuraminidase Inhibitor Oseltamivir in Treating Acute Influenza by Treanor, et al., JAMA, Feb. 23, 2000, vol. 283.

Efficacy and Safety of the Neuraminidase Inhibitor Zanamivir in the treatment of Influenza A and B Virus Infections by Monto, et al., Journal of Infectious Diseases, 1999: 180; 254-61.

Association of an increase in CD8+T cells with the presence of trypanosoma cruzi antigens in chronic human chagasic mycoarditis by Higuchi, et al., Am. J. Trop. Med. Hyg., 56(5), 1997, pp. 485-489.

The role of active myocarditis in the development of heart failure in chronic chagas disease : a study based on endomycardial biopsies by Highuci, et al., Clin. Cardiol. 10, 665-670 (1987).

A Neuraminidase from Trypanosoma cruzi removes sialic acid from the surface of mammalian myocardial and endothelial cells by Libby, et al., J. Clin. Invest., vol. 77, Jan. 1986, 127-135.

Adsorption of Mycoplasma pneumonia to neuraminic acid receptors of various cells and possible role in virulence by Sobeslavsky, et al. Journal of Bacteriology, Sep. 1968, pp. 695-705.

* cited by examiner

Figure 8A
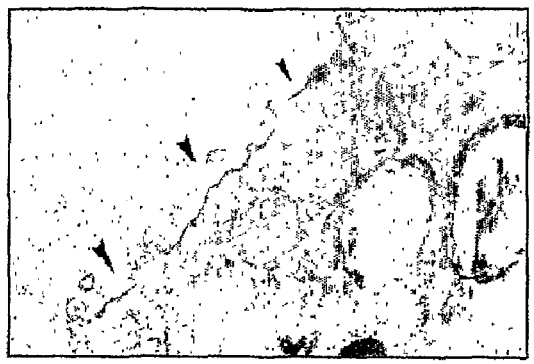
Figure 8B
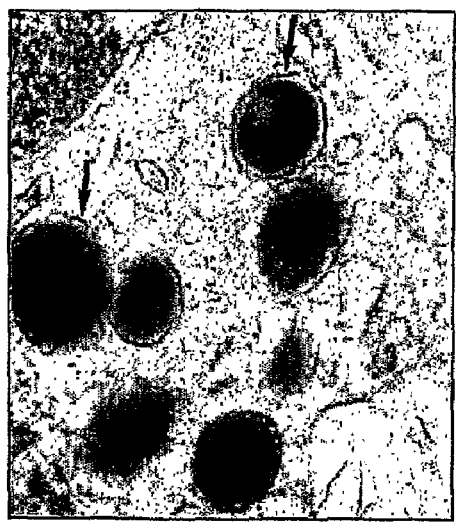
Figure 9A
Figure 9B
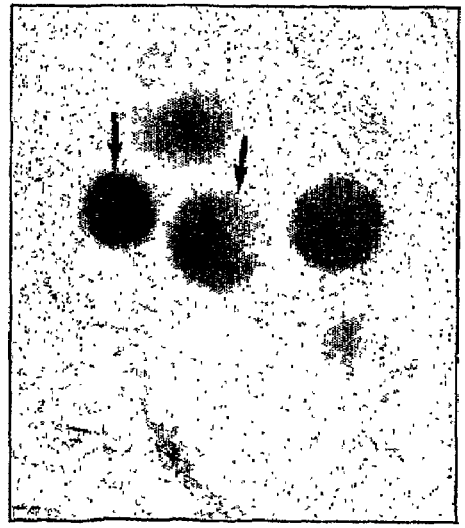

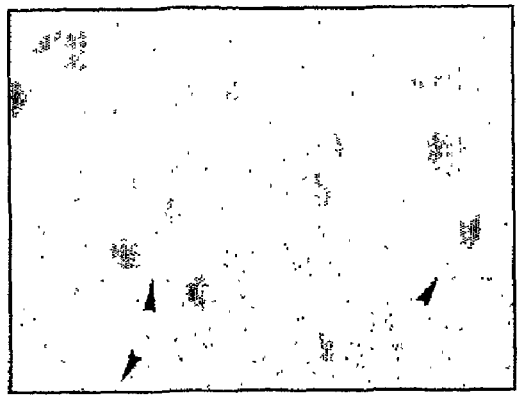
Figure 10A
Figure 10B
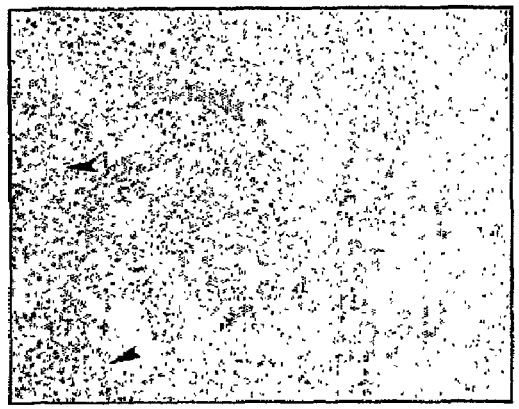
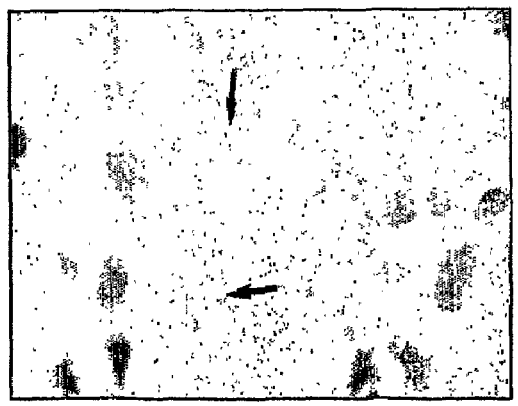
Figure 11A
Figure 11B
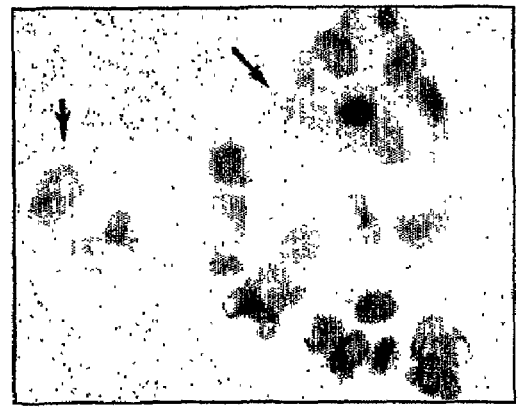

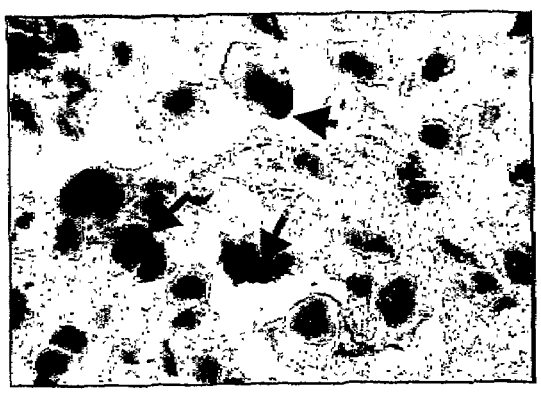
Figure 14
Figure 15
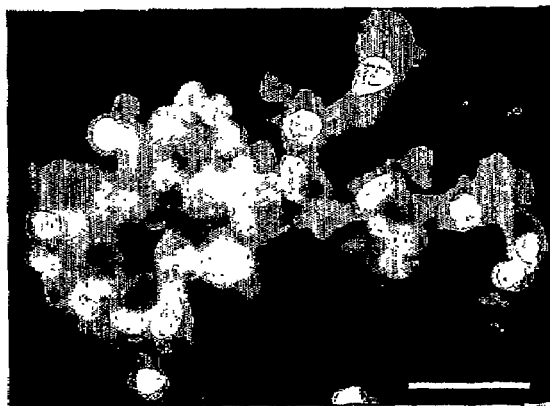
Figure 16
Figure 17
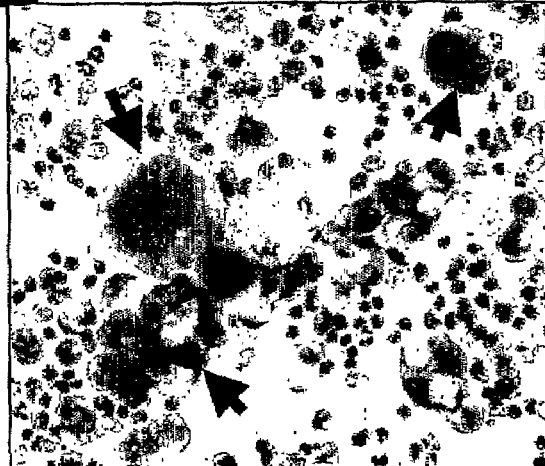

| ATGGGCAGCA | GCCATCATCA | TCATCATCAC | AGCAGCGGCC | TGGTGCCGCG | CGGCAGCCAT | 60 |
|---|---|---|---|---|---|---|
| Atggcacccg | gatcgagccg | agttgagctg | tttaagcggc | aaagctcgaa | ggtgccattt | 120 |
| gaaaagggcg | gcaaagtcac | cgagcgggtt | gtccactcgt | tccgcctccc | cgcccttgtt | 180 |
| aatgtggacg | gggtgatggt | tgccatcgcg | gacgctcgct | acgaaacatc | caatgacaac | 240 |
| tccctcattg | atacggtggc | gaagtacagc | gtggacgatg | gggagacgtg | ggagacccaa | 300 |
| attgccatca | agaacagtcg | tgcatcgtct | gtttctcgtg | tggtggatcc | cacagtgatt | 360 |
| gtgaagggca | acaagcttta | cgtcctggtt | ggaagctaca | acagttcgag | gagctactgg | 420 |
| acgtcgcatg | gtgatgcgag | agactgggat | attctgcttg | ccgttggtga | ggtcacgaag | 480 |
| tccactgcgg | gcggcaagat | aactgcgagt | atcaaatggg | ggagcccgt | gtcactgaag | 540 |
| gaattttcc | cggcggaaat | ggaaggaatg | cacacaaatc | aatttcttgg | cggtgcaggt | 600 |
| gttgccattg | tggcgtccaa | cgggaatctt | gtgtaccctg | tgcaggttac | gaacaaaaag | 660 |
| aagcaagttt | tttccaagat | cttctactcg | gaagacgagg | gcaagacgtg | gaagtttggg | 720 |
| gagggtagga | gtgattttgg | ctgctctgaa | cctgtggccc | ttgagtggga | ggggaagctc | 780 |
| atcataaaca | ctcgagttga | ctatcgccgc | cgtctggtgt | acgagtccag | tgacatgggg | 840 |
| aattcgtggg | tggaggctgt | cggcacgctc | tcacgtgtgt | ggggcccctc | accaaaatcg | 900 |
| aaccagcccg | gcagtcagag | cagcttcact | gccgtgacca | tcgagggaat | gcgtgttatg | 960 |
| ctcttcacac | acccgctgaa | ttttaaggga | aggtggctgc | gcgaccgact | gaacctctgg | 1020 |
| ctgacggata | accagcgcat | ttataacgtt | gggcaagtat | ccattggtga | tgaaaattcc | 1080 |
| gcctacagct | ccgtcctgta | caaggatgat | aagctgtact | gtttgcatga | gatcaacagt | 1140 |
| aacgaggtgt | acagccttgt | ttttgcgcgc | ctggttggcg | agctacggat | cattaaatca | 1200 |
| gtgctgcagt | cctggaagaa | ttgggacagc | cacctgtcca | gcatttgcac | ccctgctgat | 1260 |
| ccagccgctt | cgtcgtcaga | gcgtggttgt | ggtcccgctg | tcaccacggt | tggtcttgtt | 1320 |
| ggcttttttgt | cgcacagtgc | caccaaaacc | gaatgggagg | atgcgtaccg | ctgcgtcaac | 1380 |
| gcaagcacgg | caaatgcgga | gagggttccg | aacggtttga | agtttgcggg | ggttggcgga | 1440 |
| ggggcgcttt | ggccggtgag | ccagcagggg | cagaatcaac | ggtatcactt | tgcaaaccac | 1500 |
| gcgttcacgc | tggtggcgtc | ggtgacgatt | cacgaggttc | cgagcgtcgc | gagtcctttg | 1560 |
| ctgggtgcga | gcctggactc | ttctggtggc | aaaaaactcc | tggggctctc | gtacgacgag | 1620 |
| aagcaccagt | ggcagccaat | atacggatca | acgccggtga | cgccgaccgg | atcgtgggag | 1680 |
| atgggtaaga | ggtaccacgt | ggttcttacg | atggcgaata | aaattggttc | ggtgtacatt | 1740 |
| gatggagaac | ctctggaggg | ttcagggcag | accgttgtgc | cagacgggag | gacgcctgac | 1800 |
| atctcccact | tctacgttgg | cgggtatgga | aggagtgata | tgccaaccat | aagccacgtg | 1860 |
| acggtgaata | atgttcttct | ttacaaccgt | cagctgaatg | ccgaggagat | caggaccttg | 1920 |
| ttcttgagcc | aggacctgat | tggcacggaa | gcacacatgg | gcagcagcag | cggcagcagt | 1980 |
| gaaagaagta | cgcccGGATC | CGGCTGCTAA | | | | 2010 |

SEQ. NO.1

Figure 25

| | | | | | | | | | | | | | | | | | | | |
|---|---|---|---|---|---|---|---|---|---|---|---|---|---|---|---|---|---|---|---|
| Met 1 | Gly | Ser | Ser | His 5 | His | His | His | His | His 10 | Ser | Ser | Gly | Leu | Val 15 | Pro | Arg | Gly | Ser | His 20 |
| Met | Ala | Pro | Gly | Ser 25 | Ser | Arg | Val | Glu | Leu 30 | Phe | Lys | Arg | Gln | Ser 35 | Ser | Lys | Val | Pro | Phe 40 |
| Glu | Lys | Gly | Gly | Lys 45 | Val | Thr | Glu | Arg | Val 50 | Val | His | Ser | Phe | Arg 55 | Leu | Pro | Ala | Leu | Val 60 |
| Asn | Val | Asp | Gly | Val 65 | Met | Val | Ala | Ile | Ala 70 | Asp | Ala | Arg | Tyr | Glu 75 | Thr | Ser | Asn | Asp | Asn 80 |
| Ser | Leu | Ile | Asp | Thr 85 | Val | Ala | Lys | Tyr | Ser 90 | Val | Asp | Asp | Gly | Glu 95 | Thr | Trp | Glu | Thr | Gln 100 |
| Ile | Ala | Ile | Lys | Asn 105 | Ser | Arg | Ala | Ser | Ser 110 | Val | Ser | Arg | Val | Val 115 | Asp | Pro | Thr | Val | Ile 120 |
| Val | Lys | Gly | Asn | Lys 125 | Leu | Tyr | Val | Leu | Val 130 | Gly | Ser | Tyr | Asn | Ser 135 | Ser | Arg | Ser | Tyr | Trp 140 |
| Thr | Ser | His | Gly | Asp 145 | Ala | Arg | Asp | Trp | Asp 150 | Ile | Leu | Leu | Ala | Val 155 | Gly | Glu | Val | Thr | Lys 160 |
| Ser | Thr | Ala | Gly | Gly 165 | Lys | Ile | Thr | Ala | Ser 170 | Ile | Lys | Trp | Gly | Ser 175 | Pro | Val | Ser | Leu | Lys 180 |
| Glu | Phe | Phe | Pro | Ala 185 | Glu | Met | Glu | Gly | Met 190 | His | Thr | Asn | Gln | Phe 195 | Leu | Gly | Gly | Ala | Gly 200 |
| Val | Ala | Ile | Val | Ala 205 | Ser | Asn | Gly | Asn | Leu 210 | Val | Tyr | Pro | Val | Gln 215 | Val | Thr | Asn | Lys | Lys 220 |
| Lys | Gln | Val | Phe | Ser 225 | Lys | Ile | Phe | Tyr | Ser 230 | Glu | Asp | Glu | Gly | Lys 235 | Thr | Trp | Lys | Phe | Gly 240 |
| Glu | Gly | Arg | Ser | Asp 245 | Phe | Gly | Cys | Ser | Glu 250 | Pro | Val | Ala | Leu | Glu 255 | Trp | Glu | Gly | Lys | Leu 260 |
| Ile | Ile | Asn | Thr | Arg 265 | Val | Asp | Tyr | Arg | Arg 270 | Arg | Leu | Val | Tyr | Glu 275 | Ser | Ser | Asp | Met | Gly 280 |
| Asn | Ser | Trp | Val | Glu 285 | Ala | Val | Gly | Thr | Leu 290 | Ser | Arg | Val | Trp | Gly 295 | Pro | Ser | Pro | Lys | Ser 300 |
| Asn | Gln | Pro | Gly | Ser 305 | Gln | Ser | Ser | Phe | Thr 310 | Ala | Val | Thr | Ile | Glu 315 | Gly | Met | Arg | Val | Met 320 |
| Leu | Phe | Thr | His | Pro 325 | Leu | Asn | Phe | Lys | Gly 330 | Arg | Trp | Leu | Arg | Asp 335 | Arg | Leu | Asn | Leu | Trp 340 |
| Leu | Thr | Asp | Asn | Gln 345 | Arg | Ile | Tyr | Asn | Val 350 | Gly | Gln | Val | Ser | Ile 355 | Gly | Asp | Glu | Asn | Ser 360 |
| Ala | Tyr | Ser | Ser | Val 365 | Leu | Tyr | Lys | Asp | Asp 370 | Lys | Leu | Tyr | Cys | Leu 375 | His | Glu | Ile | Asn | Ser 380 |
| Asn | Glu | Val | Tyr | Ser 385 | Leu | Val | Phe | Ala | Arg 390 | Leu | Val | Gly | Glu | Leu 395 | Arg | Ile | Ile | Lys | Ser 400 |
| Val | Leu | Gln | Ser | Trp 405 | Lys | Asn | Trp | Asp | Ser 410 | His | Leu | Ser | Ser | Ile 415 | Cys | Thr | Pro | Ala | Asp 420 |
| Pro | Ala | Ala | Ser | Ser 425 | Ser | Glu | Arg | Gly | Cys 430 | Gly | Pro | Ala | Val | Thr 435 | Thr | Val | Gly | Leu | Val 440 |
| Gly | Phe | Leu | Ser | His 445 | Ser | Ala | Thr | Lys | Thr 450 | Glu | Trp | Glu | Asp | Ala 455 | Tyr | Arg | Cys | Val | Asn 460 |
| Ala | Ser | Thr | Ala | Asn 465 | Ala | Glu | Arg | Val | Pro 470 | Asn | Gly | Leu | Lys | Phe 475 | Ala | Gly | Val | Gly | Gly 480 |
| Gly | Ala | Leu | Trp | Pro 485 | Val | Ser | Gln | Gln | Gly 490 | Gln | Asn | Gln | Arg | Tyr 495 | His | Phe | Ala | Asn | His 500 |
| Ala | Phe | Thr | Leu | Val 505 | Ala | Ser | Val | Thr | Ile 510 | His | Glu | Val | Pro | Ser 515 | Val | Ala | Ser | Pro | Leu 520 |
| Leu | Gly | Ala | Ser | Leu 525 | Asp | Ser | Ser | Gly | Gly 530 | Lys | Lys | Leu | Leu | Gly 535 | Leu | Ser | Tyr | Asp | Glu 540 |
| Lys | His | Gln | Trp | Gln 545 | Pro | Ile | Tyr | Gly | Ser 550 | Thr | Pro | Val | Thr | Pro 555 | Thr | Gly | Ser | Trp | Glu 560 |
| Met | Gly | Lys | Arg | Tyr 565 | His | Val | Val | Leu | Thr 570 | Met | Ala | Asn | Lys | Ile 575 | Gly | Ser | Val | Tyr | Ile 580 |
| Asp | Gly | Glu | Pro | Leu 585 | Glu | Gly | Ser | Gly | Gln 590 | Thr | Val | Val | Pro | Asp 595 | Gly | Arg | Thr | Pro | Asp 600 |
| Ile | Ser | His | Phe | Tyr 605 | Val | Gly | Gly | Tyr | Gly 610 | Arg | Ser | Asp | Met | Pro 615 | Thr | Ile | Ser | His | Val 620 |
| Thr | Val | Asn | Asn | Val 625 | Leu | Leu | Tyr | Asn | Arg 630 | Gln | Leu | Asn | Ala | Glu 635 | Glu | Ile | Arg | Thr | Leu 640 |
| Phe | Leu | Ser | Gln | Asp 645 | Leu | Ile | Gly | Thr | Glu 650 | Ala | His | Met | Gly | Ser 655 | Ser | Ser | Gly | Ser | Ser 660 |
| Glu | Arg | Ser | Thr | Pro 665 | Gly | Ser | Gly | Cys | | | | | | | | | | | |

SEQ. NO.2

Figure 26

PREVENTION AND TREATMENT OF MYCOPLASMA-ASSOCIATED DISEASES

This application is a continuation of international application Ser. No. PCT/BR01/00083 filed Jul. 3, 2001, published in English, which claims priority to Brazilian patent applications PI0002989-0 filed Jul. 3, 2000 and PI0102648-8 filed Jul. 3, 2001.

The present invention relates to the prevention and treatment of diseases associated with undesirable cell proliferation, including atherosclerotic narrowing of blood vessels and malignancy, comprising preventing or treating infection by mycoplasma. It is based, at least in part, on the discovery that, in many cases, mycoplasma infection exists coincident with undesirable cell proliferation and/or proliferation of other infectious organisms.

BACKGROUND OF THE INVENTION

Mycoplasmas are parasites of the respiratory epithelium and urogenital tract. Although mycoplasma infections are typically asymptomatic in mammals, they seem to be cofactors in diseases, such as AIDS (Acquired Immunodeficiency Syndrome), and in sequelae after mycoplasma infections having an autoimmune basis.

Mycoplasmas are the smallest self-replicating microorganisms and have unique properties among the prokaryotes, such as (i) their need for cholesterol to maintain their membrane envelope and (ii) the absence of an external wall. Mycoplasmas are known to cause pulmonary infection in humans. See, Razin et al., "Molecular biology and pathogenicity of mycoplasmas," Microbiol. Mol. Biol. Rev.; 62(4):1094–1156, (1998). Furthermore, it is widely known that mycoplasmas can cause disease in most animals, including animals of commercial importance to the husbandry industry, such as cattle, swine, and fowl. See, Maniloff et al. Eds., Mycoplasmas, Molecular Biology and Pathogenesis, American Society for Microbiology (Washington, 1992).

It has been suggested that mycoplasma may play a role in the pathogenesis of a number of human diseases, including asthma, diseases of the large intestine, rheumatoid diseases such as rheumatoid arthritis, maculopapular erythemas, stomatitis, conjunctivitis, pericarditis, Alzheimer's Disease, multiple sclerosis, the sequelae of AIDS and HIV infection, genito-urinary infections, diseases of chronic fatigue like Chronic Fatigue Syndrome, and Gulf War Syndrome. However, the actual role of mycoplasmas in these various diseases have been difficult to determine, because most of the associations drawn to mycoplasma infection are based on serologic evidence rather than direct observation of mycoplasma organisms in disease lesions. See, Cole, "Mycoplasma interactions with the immune system: implications for disease pathology," (http://www.compkarori.com/arthritis/pi16002.htm); Cole, "Mycoplasma-induced arthritis in animals: relevance to understanding the etiologies of the human rheumatic diseases," Rev. Rhum. Engl. Ed.; 66(1 Suppl):45S–49S (1999); and Nicolson et al., "Mycoplasmal infections in chronic illnesses," (http://www.gulfwarvets.com/article24.htm).

Mycoplasma as well as chlamydia have been implicated in vascular disease, but the etiologic relationships have not been confirmed. See, Chen et al., "Carditis associated with Mycoplasma pneumoniae infection," Am. J. Dis. Child. 140:471–472 (1986); Clyde et al., "Tropism for Mycoplasma gallisepticum for arterial walls," Proc. Natl. Acad. Sci. U.S.A. 70: 1545–1549 (1973); Danesch et al., "Chronic infections and coronary artery disease: is there a link?", Lancet 350:430–436 (1997); Farraj et al., "Mycoplasma-associated pericarditis, case report," Mayo Clin. Proc. 72:33–36 (1997); Fu et al., "Middle cerebral artery occlusion after recent Mycoplasma pneumoniae infection," J. Neurol. Sci. 157:113–115 (1998); Gurfinkel et al., "IgG antibodies to chlamydial and mycoplasma infection plus C-reactive protein related to poor outcome in unstable angina," Arch. Inst. Cardiol. Mex. 67:462–468 (1997); Ong et al., "Detection and widespread distribution of Chlamydia pneumoniae in the vascular system and its possible implications," J. Clin. Pathol. 49:102–106 (1996); Perez et al., "Leukocytoclastic vasculitis and polyarthritis associated with Mycoplasma pneumoniae infection," Clin. Infect. Dis. 25:154–155 (1997); Taylor-Robinson and Thomas, "Chlamydia pneumoniae in arteries: the facts, their interpretation, and future studies," J. Clin. Pathol. 51:793–797 (1998). In Maraha et al., "Is Mycoplasma pneumoniae associated with vascular disease," J. Clin. Microbiol. 38:935–936 (February 2000), it was stated that "in a serological study, in contrast to C. pneumoniae antibodies, M. pneumoniae antibodies are not associated with recurrent events in patients with unstable angina", citing Gurfinkel et al., supra. Maraha et al. reported that using PCR, they "were unable to detect M. pneumoniae in the great majority of the 103 tested specimens" of atherectomies and degenerative heart valves, and concluded that "the results . . . do not support the hypothesis that M. pneumoniae is an important factor in the development of vascular disease." In contrast, Horne et al. have published a correlation between a positive serology for Mycoplasma pneumoniae and atherosclerosis (Horne et al., "IgA sero-positivity to Mycoplasma pneumoniae predicts the diagnosis of coronary artery disease," J. Am. Coll. Cardiol. 35:321 (abstract) (2000)).

The co-occurrence of mycoplasma and other infectious agents seems to increase the virulence of both pathogens. For example, HIV patients, who have positive serology for Mycoplasma penetrans, are in worse clinical health than HIV patients who test negative for Mycoplasma penetrans. See, Blanchard et al., "AIDS-associated mycoplasmas," Annu. Rev. Microbiol., 48:687–712, (1994).

Morphological studies of pathogenic mycoplasma indicate that these microorganisms which, unlike bacteria, lack cell walls, are strongly attached to the external surface of host cells through their membranes. This attachment is apparently the first step for colonization of a target tissue and a prerequisite for infection, as disclosed in Collier and Clyde, "Relationships between M. pneumoniae and human respiratory epithelium," Infect. Immun., 3:694–701 (1971), and Kahane et al., "Attachment of mycoplasmas to erythrocytes: a model to study mycoplasma attachment to the epithelium of the host respiratory tract," Isr. J. Med. Sci., 17:589–592 (1981). Moreover, experimental studies have demonstrated that mycoplasmas that were attached to macrophages could not be reached by different concentrations of complement, suggesting that cellular attachment may protect the mycoplasma, from the natural defense mechanisms of the host. See, Bredt et al., "Adherence of mycoplasmas: phenomena and possible role in the pathogenesis of disease," Infection, 10(3):199–201 (1982), and Kahane, "Purification of attachment moiety: a review," Yale J. Biol. Med., 53:665–669 (1983).

Accordingly, prevention of or interference with the first step of mycoplasma attachment can provide an important means of controlling infection. Currently existing antibiotics, however, have been ineffective at either preventing or breaking the adhesion of pathogenic mycoplasmas to the host cells.

The attachment zone of Mycoplasma pneumoniae ("M. pneumoniae") and of other mycoplasmas is rich in glycoproteins that contain sialic acid. See, Chandler et al., "Mycoplasma pneumoniae attachment: competitive inhibition by mycoplasmal binding component and by sialic acid-containing glycoconjugates," *Infect. Immun.*, 38(2):598–603 (1982), Glasgow and Hill, "Interactions of Mycoplasma gallisepticum with sialyl glycoproteins," *Infect. Immun.*; 30:353–361 (1980), and Hansen et al., "Characterization of hemadsorption-negative mutants of Mycoplasma pneumoniae," *Infect. Immun.*, 32:127–136 (1981). Electron microscopy observations have indicated that glycoproteins linked to sialic acid mediate the attachment and the virulence of Mycoplasma pulmonis ("M. pulmonis") in rats. See, Taylor-Robinson et al., "Mycoplasmal adherence with particular reference to the pathogenicity of Mycoplasma pulmonis," *Isr. J. Med. Sci.*, 17:599–603 (1981). Although mycoplasmas may attach to regions without the host cell sialic acid, the presence of sialic acid at the adhesion site may be essential for mycoplasmas to become virulent. See, Krause et al., "Identification of Mycoplasma pneumoniae proteins associated with hemadsorption and virulence," *Infect. Immun.*, 35:809–817 (1982), and Baseman et al., "Sialic acid residues mediate Mycoplasma pneumoniae attachment to human and sheep erythrocytes," *Infect. Immun.*, 38(1):389–391 (1982). This attachment zone is sensitive to pronase and can be inactivated by neuraminidase, as disclosed in Gabridge and Taylor-Robinson, "Interaction of Mycoplasma pneumoniae with human lung fibroblasts: role of receptor sites," *Infect. Immun.*, 25:455–459 (1979).

Sialic acid was initially discovered on the surface of *Trypanosoma cruzi* ("*T. cruzi*") by Pereira et al. in 1980. See, Pereira et al., "Lectin receptors as markers for *Trypanosoma cruzi*. Development stages and a study of the interaction of wheat germ agglutinin with sialic acid residues on epimastigotes cells," *J. Exp. Med.*, 152:1375–92 (1980). Pereira also first demonstrated in 1983 that *T. cruzi* has sialidase activity. See, Pereira, "A developmentally regulated neuraminidase activity in *Trypanosoma cruzi*," *Science*, 219:1444–46 (1983).

Trans-sialidase, an enzyme expressed on the *T. cruzi*'s surface, catalyzes the transfer of sialic acid from host glycoconjugates to glycoprotein molecules on the surface of the parasite. See, Schenkman et al., "Attachment of *Trypanosoma cruzi* trypomastigotes to receptors at restricted cell surface domains," *Exp. Parasitol.*, 72:76–86 (1991). The enzyme is present both in the epimastigote form (i.e., in the invertebrate vector) and in the trypomastigote form (i.e., infectious form that circulates in the blood of the vertebrate host). See, Agusti et al., "The trans-sialidase of *Trypanosoma cruzi* is anchored by two different lipids," *Glycobiology*, 7(6):731–5, (1997).

The catalytic portion of trans-sialidase ("TSC") has two kinds of enzymatic activity: (1) neuraminidase activity, which releases sialic acid from the complex carbohydrates; and (2) sialil-transferase activity, which catalyzes the transfer of sialic acid from glycoconjugate donors to terminal β-D galactose containing acceptors. See, Scudder et al., "Enzymatic characterization of beta-D-galactoside alpha 2,3-trans-sialidase from *Trypanosoma cruzi*" *J. Biol. Chem.*, 268(13):9886–91 (1993).

In the complete native form of trans-sialidase ("TSN"), the enzyme has a C-terminal extension having a repetitive sequence of 12 amino acids previously identified as SAPA (i.e., Shed-Acute-Phase-Antigens). Although the repetitive sequence of amino acids is not directly involved in the catalytic activity, it stabilizes the trans-sialidase activity in the blood to increase the half-life of the enzyme from about 7 to about 35 hours. See, Pollevick et al., "The complete sequence of SAPA, a shed acute-phase antigen of *Trypanosoma cruzi*," *Mol. Biochem. Parasitol.* 47:247–250 (1991) and Buscaglia et al., "The repetitive domain of *Trypanosoma cruzi* trans-sialidase enhances the immune response against the catalytic domain," *J. Infect. Dis.*, 177(2):431–6 (1998).

In the plasma membrane of *T. cruzi* trypomastigotes, the sialic acid acceptors are involved in the adherence of the parasite to the host and its subsequent invasion into the cell. Trans-sialidase may also sialylate the host cell glycoconjugates, forming receptors that will be used by the trypomastigotes for the attachment and penetration into the target cells.

The trans-sialidase enzyme of *T. cruzi* has been well characterized. See, Pollevick et al., *Mol. Biochem. Parasitol.* 47:247–250 (1991); Pereira et al., *J. Exp. Med.* 174:179–192; Schenkman et al., "*Trypanosoma cruzi* trans-sialidase and neuraminidase activities can be mediated by the same enzyme," *J. Exp. Med.* 175:567–575 (1992); Schenkman et al., "Structural and functional properties of *Trypanosoma* trans-sialidase," *Annu. Rev. Microbiol.* 48:499–523 (1994); Schenkman et al., "A proteolytic fragment of *Trypanosoma cruzi* trans-sialidase lacking the carboxy-terminal domain is active, monomeric, and generates antibodies that inhibit enzymatic activity" *J. Biol. Chem.* 269:7970–7975 (1994); Campetella et al., "A recombinant *Trypanosoma cruzi* trans-sialidase lacking the amino acid repeats retains the enzymatic activity," *Mol. Biochem. Parasitol.* 64:337–340 (1994); Parodi et al., "Identification of the gene(s) coding for the trans-sialidase of *Trypanosoma cruzi*" *EMBO J.* 11:1705–1710 (1992); Uemura et al., "Only some members of a gene family in *Trypanosoma cruzi* encode proteins that express both trans-sialidase and neuraminidase activities," *EMBO J.* 11:3837–3844 (1992); Cremona et al., "A single tyrosine differentiates active and inactive *Trypanosoma cruzi* trans-sialidase," *Gene* 160:123–128 (1995).

The enzymatically active protein extracted from the *T. cruzi* trypomastigotes has 4 distinct amino acid regions: (1) a N-terminal region with approximately 380 amino acids of which 30% of the sequence is similar to bacterial sialidases; (2) a region with approximately 150 residues that does not show any similarity with any known sequence; (3) a region with homology to type III fibronectin (FnIII); and (4) a C-terminal region containing 12 repeated amino acids, which is the immuno-dominant portion and which is required for enzyme oligomerization. The N-terminal and the FnIII regions are important for trans-sialidase activity.

Native and purified trans-sialidase ("TS") form multi-numerical aggregates having a molecular weight of more than 400 kDA. These aggregates are linked to the surface of the parasite membrane through a GPI anchor and are only released to the external medium through phospholipase C. After being denatured, the multi-numerical aggregates of TS migrate in a SDS-PAGE gel forming multiple bands ranging from about 100 to about 220 kDA.

SUMMARY OF THE INVENTION

The present invention relates to methods and compositions for the prevention and treatment of disorders caused by mycoplasma infection. It is based, at least in part, on the discovery that mycoplasma infection is associated with disorders of increased cell proliferation, including arterial atheromas and various malignant neoplasic tissues. It was further noted that in many cases such atheromas and malignant tissues were also infected with chlamydia organisms.

Accordingly, the present invention provides for methods of preventing and/or treating disorders manifested by increased cell proliferation and/or co-existent proliferation of other infectious organisms whereby a subject is administered an effective amount of an agent which prevents or inhibits mycoplasma infection. The agent may be an antibiotic, but, in preferred embodiments of the invention, the agent is a protein capable of removing sialic acid residues, such as a neuranimidase enzyme or, more preferably, a trans-sialidase enzyme, wherein removal of sialic acid inhibits or prevents the attachment of mycoplasma to host cells. In particularly preferred embodiments of the invention, the agent is the trans-sialidase enzyme of *Trypanosoma cruzi*, or a portion or variant of the native enzyme which has trans-sialidase activity. This aspect of the invention is based, at least in part, on the discovery that patients suffering from infection with *Trypanosoma cruzi* exhibited less atherosclerotic coronary artery disease and less mycoplasma in the intima.

The disorders to be treated according to the invention include, but are not limited to, atherosclerosis and malignancy. Without being bound to any particular theory, it is hypothesized that infection with mycoplasma may inhibit programmed cell death (apoptosis).

DESCRIPTION OF THE FIGURES

FIG. 1A—Endothelial cell (End) of vasa vasorum exhibiting very small forms of Mycoplasma pneumoniae (MP) adhered to the endothelial surface. Presence of an elementary body of Chlamydia pneumoniae (CP) in the cytoplasm (original magnification: 3,300×). FIG. 1B—Adventitial macrophage containing several CP bodies and MP forms (2,600×). FIG. 1C—Necrotic core of atheroma plaque exhibiting many CP bodies and MP forms among abundant ruptured membrane elements (4,200×). FIG. 1D—Two ellipsoid forms of MP in the interstitium (10,000×). FIG. 1E—Several positive rounded brownish structures of MP inside a vulnerable plaque (1,000×). FIG. 1F—Closer view of a necrotic atheromatous core exhibiting many positive brownish dots corresponding to MP (1,000×).

In FIG. 7A, the mycoplasmas (in green) are larger, with prolongations that reach the spaces between the cells that are visible the red colored nuclei (stained with iodide propidium). In FIG. 7B that represents rat D, the mycoplasmas are smaller and lack prolongations (acquired at 630×magnification).

FIGS. 8A and 8B—Show ultrastructural aspects of the lungs from rats A and D, respectively. FIG. 8A shows that in rat A, the alveolar surface is completely covered by mycoplasmas (arrowheads). The same does not occur on the surface of the alveoli of rat D (arrowheads; FIG. 8B) (×3,300—original magnification).

FIGS. 9A and 9B—Reveal aspects of to C. pneumoniae (arrows) by electron microscopy in rats A and D respectively. In rat D, the C. pneumoniae are losing their membrane and are degenerating, as compared to those in rat A (×10,000—original magnification).

FIG. 10A—Refers to rat A, showing a large number of macrophages containing C. pneumoniae antigens (in brown—arrowheads) in the lymphoid nodes at the peribronchial sites (Immunoperoxidase—against C. pneumoniae—× 1,000).

FIG. 10B—Refers to rat F (a severely affected female rat treated for 9 days with Native TS), showing large numbers of plasma cells positive for C. pneumoniae antigens (in brown—arrows) at the periphery of the peribronchial lymphoid nodes. (Immunoperoxidase against C. pneumoniae, ×160). However, the alveoli are free of C. pneumoniae.

FIG. 11A—Refers to rat A, seen in a higher magnification view, showing granules of C. pneumoniae in the macrophage cytoplasm, and in the extracellular space (immunoperoxidase against C. pneumoniae—in brown—arrows—×1, 000).

FIG. 11B—Refers to rat F (treated for 9 days with Native TS) showing macrophages in the alveolar septa containing cytoplasmic C. pneumoniae antigens with a hyaline aspect suggesting degenerated bacteria (Immunoperoxidase against C. pneumoniae—in brown—arrows—×1,000).

FIG. 14—Presence of Mycoplasma pneumoniae DNA (arrows indicating brown stained regions) in neoplasic cells and in inflammatory cells from a transitional cell carcinoma from bladder, invasive, undifferentiated form. (in situ hybridization technique—Original magnification 100×).

FIG. 15×Cytological exam of ascites fluid from a patient with ovarian adenocarcinoma, exhibiting malignant neoplasic cells stained in brown due to the presence of M. pulmonis antigens, mainly on the surface, frequently forming fibrilar tufts (arrows). (Immunohistochemistry against M. pulmonis—Original magnification 100×).

FIG. 16—Culture of neoplasic cells from the ascites fluid described above and doubled stained: M. pneumoniae antigens in green (fluorescein) occupy almost all the cytoplasm; nuclei in red are stained with Cy-5. Superposition of the green and red label is shown in yellow. (Laser confocal microscopy technique—original magnification 100×).

FIG. 17—Cytological exam of ascites fluid from the same patient mentioned above, showing neoplasic cells forming clumps; the cells are frequently multinucleate. (Papanicolaou stain—Original magnification—100×).

FIG. 25—Nucleotide sequence of plasmid encoding the catalytic trans-sialidase unit of trans-sialidase from *T. cruzi* (SEQ ID NO:1). The letters in capital represent the pET14 B and the underlined correspond to the oligonucleotideos' position.

FIG. 26—Amino acid sequence of the protein encoded by the nucleic acid sequence depicted in FIG. 25.(SEQ ID NO:2). In bold are the aminoacids not found in the original clone.

DETAILED DESCRIPTION OF THE INVENTION

Figure 1A:
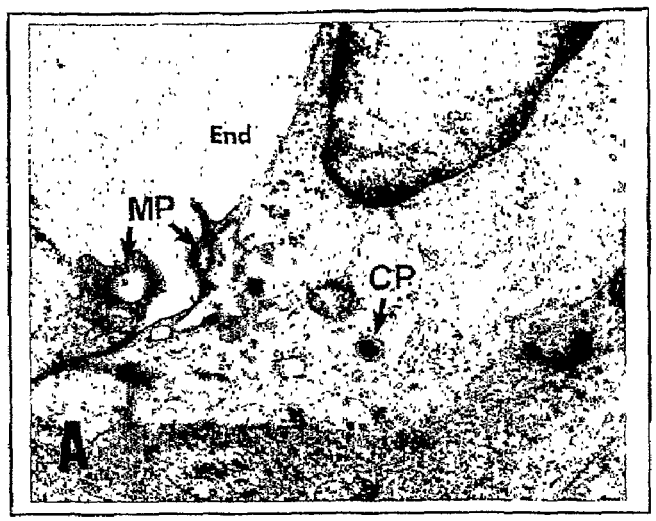
FIGS. 1A–F—Electron microscopy (A–D) and histopathological view of in situ hybridization with a M. pneumoniae bioprobe (E,F) of fatal ruptured plaque coronary artery segments.

The present invention relates to methods and compositions for preventing and/or treating conditions characterized by increased cell proliferation and/or increased proliferation of non-mycoplasma microbes and associated with mycoplasma infection. The methods comprise the administration of an effective amount of an agent which prevents or decreases mycoplasma infection. Preferably, where mycoplasma infection already exists, the level of infection is decreased by at least ten percent. The level of infection may be measured by the number of mycoplasma organisms present in a tissue or fluid sample, by the immune reaction toward mycoplasma in the subject, or by any standard laboratory mycoplasma diagnostic assay.

The subject of the invention may be a human or a non-human subject, and the term "mycoplasma" as used herein may refer to mycoplasma capable of infecting a human and/or a non-human host. Where the host is a human, the mycoplasma may be, for example but not by way of limitation, Mycoplasma (M.) *buccale, M. faucium, M. fermentans, M. Genitalium, M. hominis, M. lipophilum, M. oral, M. penetrans, M. pneumoniae, M. salivarium,* or *M. spermatophilum.*

The agent used to prevent or decrease cell proliferation associated with mycoplasma infection may be an antibiotic or non-antibiotic agent. Where the agent is an antibiotic, it may be, for example but not by way of limitation, erythromycin, azithromycin, clarithromycin, tetracycline, doxycycline, minocycline, clindamycin, ofloxacin, chloramphenicol, or any antibiotic known to have activity against mycoplasma. The dose of antibiotic may be the standard dose or a lower dose.

In preferred embodiments of the invention, the agent is not an antibiotic but rather is an agent which is able to interfere with the attachment of mycoplasma to their host cells via sialic acid residues. For example, the agent may exhibit neuraminidase and/or trans-sialidase activity. The source of such activity may be, for example, a eukaryotic or prokaryotic neuraminidase and/or trans-sialidase enzyme, or an enzymatically active fragment or mutant thereof. Where the enzyme is a neuramindase, the amount of neuraminidase to be administered may be between about $1\times10^{-2}$ to $1\times10^{3}$ U per day, where a unit of enzyme activity is defined as 1 nmol of 4-MuNana hidrolyzed in one minute at 37° C. in the presence of 0,5 mM of 4-MuNana. See, Ribeirão e cols., "Temperature differences for trans-glycosylation and hydrolysis reaction reveal an acceptor binding site in the catalytic mechanism of *Trypanosoma cruzi* trans-sialidase", *Glycobiology,* 7:1237–1246 (1997).

In specific preferred embodiments of the invention, the agent is trans-sialidase from the microorganism *Trypanosoma cruzi.* The trans-sialidase enzyme of this microorganism is well characterized, and active fragments of the enzyme are known (for various references, please refer to the Background section, supra).

For example, in particular embodiments of the invention, native trans-sialidase of *T. cruzi* may be utilized. Such enzyme may be comprised in the supernatant of a *T. cruzi*-infected cell culture, prepared by standard techniques and preferably sterilized (e.g., by filtration). See Umezawa et al., "Immunoblot assay using excreted/secreted antigens of *Trypanosoma cruzi* in serodiagnosis of congenital, acute and chronic Chagas' disease," *J. Clin. Microbiol.,* 34: 2143–2147, 1996 (USA) e Umezawa e cols., "Enzyme-linked immunosorbent assay with *Trypanosoma cruzi* excreted-secreted antigens (TESA-ELISA) for serodiagnosis of acute and chronic Chagas' disease," *Diagn. Microbiol. Infect. Dis.* 39: 169–176, 2001 (USA). Alternatively, such enzyme may be purified from a supernant of *T. cruzi*-infected cell culture by standard techniques. See, Schenkman S et al., "*Trypanosoma cruzi* trans-sialidase and neuraminidase activities can be mediated by the same enzymes," *J Exp Med* 175(2): 567–575 (1992). As still another alternative, recombinant full-length or partial-length *T. cruzi* trans-sialidase may be expressed and purified using standard genetic engineering techniques. The GenBank accession number for the *T. cruzi* trans-sialidase is D50685.

In a particularly preferred embodiment of the invention, a portion of the native *T. cruzi* trans-sialidase containing the catalytic portion ("TSC") is utilized. For example, the following construct, as developed by Dr. Sergio Schenkman, may be used. The expression vector has the advantage of producing high yields of protein. The TSC protein has the advantages of (1) lower immunogenicity (due to lack of the repeat-containing domain); (2) a shorter half-life and (3) a His-tag, which facilitates purification.

The trans-sialidase gene may be obtained from a genomic clone, isolated from a lambda Zapll library (Stratagene, http://www.stratagene.com) of *T. cruzi* Y strain (Silva and Nussenzweig, Folia Clin Biol 20:191–203 (1953), as described in Uemura et al., EMBO J 11:3837–3844 (1992). From the original lambda clone, which express enzymatic activity, a SK plasmid containing the trans-sialidase gene was generated (SK-154-0). The preferred plasmid used is termed pTSII, and corresponds to a fragment of the original gene (clone 154-0) inserted into the sites NdeI and BamHI of the vector pET14b (Novagen—http://www.novagen-.com). The pTSII was constructed by the following procedure: By using SK-154-0 as template and TSPET14 (5'-GGAATTCCATATGGCACCCGGATCGAGC, SEQ ID NO:3) and RT 154 (5'-CGGATCCGGGCGTACT-TCTTTCACTGGTGCCGGT, SEQ ID NO:4) a PCR product was amplified having a sequence as set forth in FIG. 25. The corresponding amino acid sequence is depicted in FIG. 26. The final plasmid may be transformed into the bacteria *Escherichia coli* BLB21 DE3. The construct may be made in two steps because there is an internal BamHI site in the gene. The PCR product may be treated with BamHI and NdeI enzymes, the resulting fragments fractionated in agarose gel electrophoresis, and then purified from the gel with Sephaglass (Amersham-Pharmacia) purification kit. So the 5' fragment NdeI-BamHI may be inserted into the pET14b vector pre-digested with BamHI and NdeI. The ligation products may be transformed into *E. coli* K12 DH5α, selected and the expected plasmid purified. Then this intermediate plasmid construct may be treated with BamH1, shrimp alkaline phosphatase and ligated with BamHI-BamHI-3' fragment purified from the gel mentioned above. The ligation products again may be transformed into *E. coli* K12 DH5α, selected and the expected plasmid purified. The final plasmid may be confirmed by restriction analysis and used to transform the BLB21 DE3 pLys strain.

Alternatively, other *E. coli* vectors may be used. The original gene was discovered by three laboratories (Pollevick et al., *Mol. Biochem. Parasitol.* 47:247–250 (1991); Pereira et al., *J. Exp. Med.* 174:179–191 (1991) and Uemura et al., *Embo J.* 11:3837–3844 (1992)). Other references disclose other constructs to prepare trans-sialidase, including Schenkman et al., *J. Biol. Chem.* 269:7970–7975 (1994); Buschiazzo et al., *Cell Mol. Biol.* 42:703–710 (1996); Campetella et al., *Mol. Biochem. Parasitol.* 64:337–340 (1994); Cremona et al., *Mol. Biochem. Parasitol.* 160:123–128 (1995); Cremona et al., *Cell. Mol. Biol.* 42:497–702 (1996); and Laroy et al., *Protein Expr. Purif.* 20:389–393 (2000). The purification of recombinant trans-sialidase (TSC) may be done basically as described bellow: Aliquots frozen at −70 C containing *E. coli* BLB 21DE3 pLys, and the plasmid pTSII (0.5 ml) may be inoculated in 50 ml LB medium containing 50 ug/ml carbenicillin and 34 ug/ml chloramphenicol. After an overnight incubation at 37° C. under agitation, the 50 ml culture may be inoculated in 2 liter LB medium containing 50 ug/ml carbenicillin. The cultures may be maintained at 37 C under agitation, until the absorbance at 600 nm reaches 0.5, when the cultures are shifted to 30 C and the bacteria induced by addition of 0.5 mM isopropyl-β-D-thio-galactopyranoside. After growing for more 18–20 hs, the bacteria may be collected by centrifugation, resuspended in 50 mM sodium phosphate buffer, pH 7, containing 0.3 M NaCl, 0.1 mM dithiothreitol, 1 mM phenyl-methyl-sulfonyl-fluride, 10 ug/ml leupeptin, 1 ug/ml antipain. The bacteria may be lysed by sonication (3 to 4 cycles of 5 min each) at 4° C. After the remotion of insoluble material by centrifugation at 10000×g, 1 h at 4 C, the enzyme may be purified by a NiTA-Agarose (Qiagem) and ion exchange chromatography by using a MonoQ column as described as described by Ribeirão et al., "Temperature differences for trans-glycosylation and hydrolysis reaction reveal an acceptor binding site in the catalytic mechanism of *Trypanosoma cruzi* trans-sialidase". *Glycobiology,* 7:1237–1246, 1997.

The amount of trans-sialidase activity required to confer a therapeutic benefit may vary from patient to patient and depending on the nature of the condition to be treated. Thus, the doses set forth below may require adjustment as would be apparent to the skilled artisan.

The present invention provides for methods of inhibiting undesirable cell proliferation comprising administering, to a subject in need of such treatment, an amount of trans-sialidase effective in inhibiting cell proliferation and/or in decreasing the level of mycoplasma infection. Preferably the level of cell proliferation and/or the level of mycoplasma infection is decreased by at least ten percent. Where the trans-sialidase activity is administered as a native enzyme, the amount of enzyme administered may be between 140 and 2,000 units per day.

Each trans-sialidase unit is defined as follows: in a standard trans-sialidase reaction, made in 50 ul of 20 mM Hepes pH 7.0 buffer, 0.2% BSA and 0.36 nmol ($^{14}C$)-lactose (7.2 uM) (60 mCi/mmol), and 50 nmol (1 mM) sialyl-lactose at 25 C, one Unit of trans-sialidase activity is defined as the transfer of 0.36 nmol of sialic acid from unlabeled sialyl-lactose to the ($^{14}C$) lactose in 30 min under the above conditions. This corresponds to the incorporation of sialic acid into $^{14}C$-lactose given 30000 CPM, detected by liquid scintillation counting after dilution of the reaction mixture with 1 ml water, passage of the mixture through a 0.5 ml QAE-Sephadex A25 column (equilibrated in water), and elution of the formed ($^{14}C$) siallyllactose with 1 ml of 1 M ammonium formate.

Where the trans-sialidase activity is administered in the form of a recombinant enzyme comprising a catalytic subunit of a native trans-sialidase enzyme, such as the TSC enzyme, the amount of enzyme administered may be between $10^6$ and $10^{13}$ units per day. Higher TSC doses may be used because its clearance is much faster than TSN. This occurs because TSC has no 12 amino acid C-terminal repeats; See, Buscaglia et al., "Tandem amino acid repeats from *Trypanosoma cruzi* shed antigens increase the half-life of proteins in blood", *Blood,* 93:2025–2032, 1999. In a preferred, specific embodiment of the invention, 4 mg TSC per day (preferably corresponding activity of $3.4 \times 10^7$ U) may be administered over a two week period, or until a desired clinical effect, or undesirable side effects occur. In an alternative preferred embodiment, a supernatant of a *T. cruzi* culture, with a mean trans-sialidase activity of about 140 U/day, may be administered every other day for one week, or until a desired clinical effect, or undesirable side effects occur.

The period of treatment may be for one day or may extend for an indefinite period of time, including continuous use for years. Preferably, the treatment period is between 1 week and 8 weeks.

The route of administration may be intravenous, intraperitoneal, intrathecal, oral, by inhalation, subcutaneous, intramuscular, or any other appropriate route.

The agent of the invention may be comprised in a suitable pharmaceutical vehicle. It may be used together with other agents directed toward treating either the mycoplasma infection or the undesirable cell proliferation. As a specific example, an agent having neuraminidase and/or trans-sialidase activity may be used in conjunction with, for the treatment of atherosclerotic vascular disease, an anti-platelet or anti-thrombotic agent or, for the treatment of a malignancy, a standard chemotherapeutic agent or radiation therapy.

Disorders characterized by undesirable cell proliferation include atherosclerotic vascular disease (for example of the coronary arteries, carotid arteries, cerebral vasculature, aorta, etc.), and malignancies including but not limited to ovarian carcinoma, breast cancer, prostate cancer, colon cancer, lung cancer (small cell and non-small cell varieties, mesothelioma, etc.), pancreatic cancer, gastric cancer, thyroid cancer, melanoma, leukemia, Hodgkin's lymphoma, non-Hodgkin's lymphoma, testicular carcinoma, etc.

The agent of the invention may also be used to treat disorders characterized by co-infection with mycoplasma and at least one other microbe, where the microbe may be a virus (e.g., Human Immunodeficiency Virus) or bacterium (e.g. a chlamydia). The amount of agent administered is an amount which inhibits or prevents mycoplasma adhesion and/or infection.

EXAMPLE 1

Association of Mycoplasma Infection with Atherosclerosis of Coronary Arteries

It was shown, using electron microscopy, in situ hybridization and immunohistochemical techniques, that Mycoplasma pneumoniae is related to the presence of atherosclerosis in coronary arteries. It was also demonstrated that large numbers of Chlamydia pneumoniae are present in the atheromatous plaques possibly leading to plaque rupture and thrombosis. The proliferation of chlamydia appears to be a consequence of the close association between this bacterium and mycoplasmas, which results in inflammation and rupture of the atheromatous plaque in the coronary arteries of patients who had died due to acute myocardial infarction. These data were obtained by analyzing autopsy material.

In particular, four groups of coronary artery segments were compared: 1) segments with ruptured and thrombosed atheromas from patients who died of acute myocardial infarction; 2) segments with stable plaques from the same patients of group 1 exhibiting an equivalent degree of obstruction; 3) segments with stable severely obstructive plaque from patients who died from a cause other than acute myocardial infarction; and 4) segments from non-atherosclerotic patients. In this latter group, several autopsy cases from chagasic patients (patients suffering from *Trypanosoma cruzi* infection) who died of chronic heart failure were included as we noticed that chronic chagasic patients usually do not present severe atherosclerosis. We found mycoplasmas to be absent or minimal in the intimal layer of the coronary artery segments of non-atherosclerotic patients, which contrasts with the high concentration in the intimal layer of the coronary arteries of atherosclerotic patients.

This study also showed that Chlamydia pneumoniae was present in the majority of the segments of the 4 groups of coronary arteries, although to a much greater degree in the group exhibiting ruptured and thrombosed plaque segments.

Figure 1B:
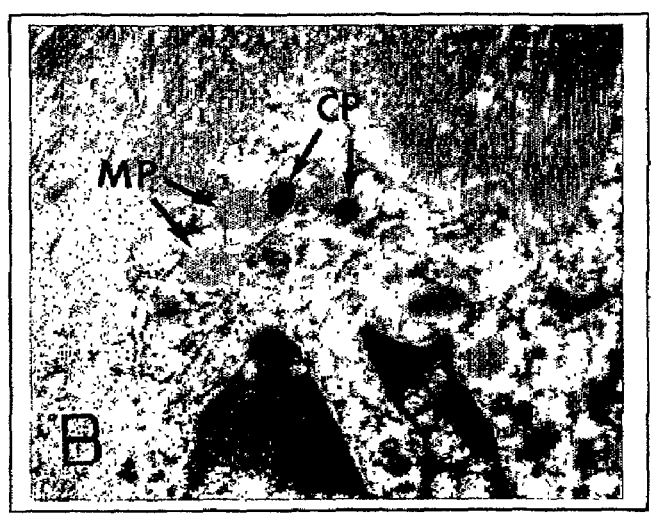
Figure 1C:
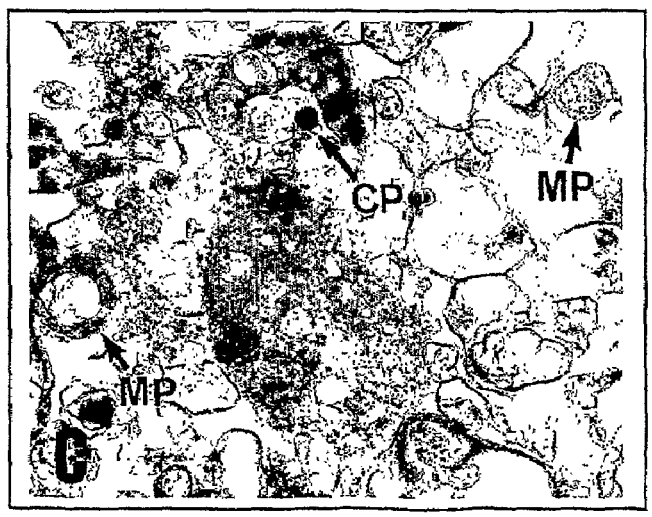
Figure 1D:
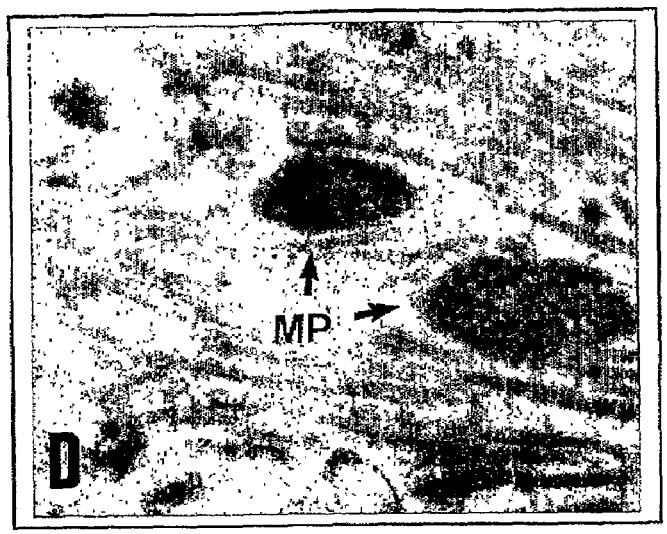
Figure 1E:
Figure 1F:
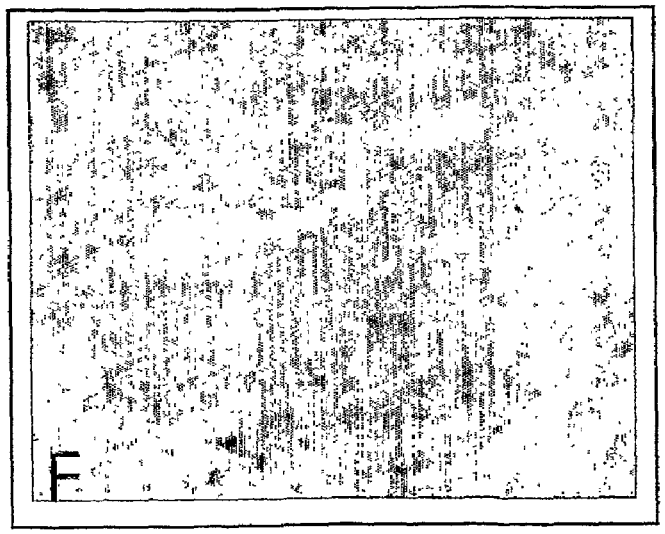
Figure 2A:
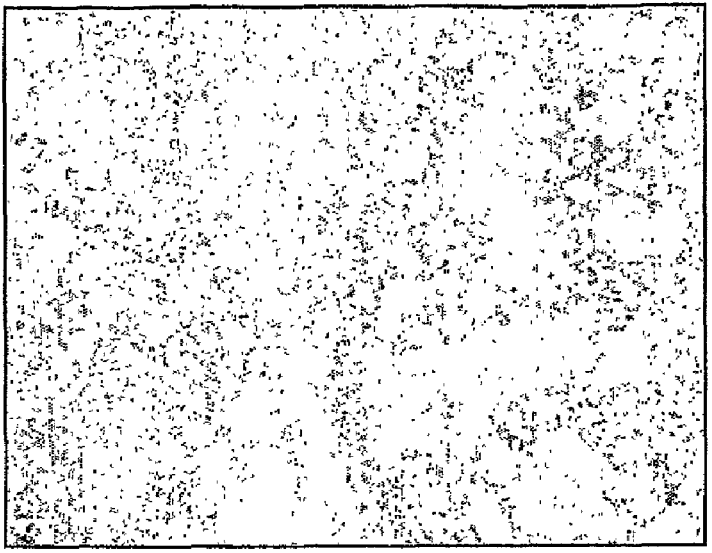
FIG. 2A—Illustrates a microscopic aspect of rat A (non-treated animal), showing severe chronic bronchitis and interstitial pneumonitis (H&E—×63—original magnification).
Figure 2B:
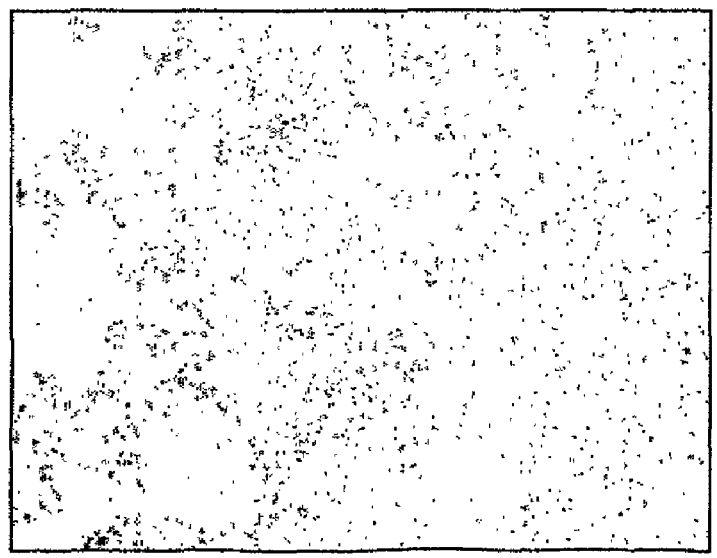
FIG. 2B—Shows rat D (after being treated for 7 days with Catalytic TS), revealing resolving interstitial pneumonitis. (H&E×100)
Figure 3A:
FIG. 3A—Illustrates rat A with interstitial pneumonitis seen in a high magnification view, showing vacuolated macrophages that correspond to C. pneumoniae infected cells (arrows)—H&E×1,000.
Figure 3B:
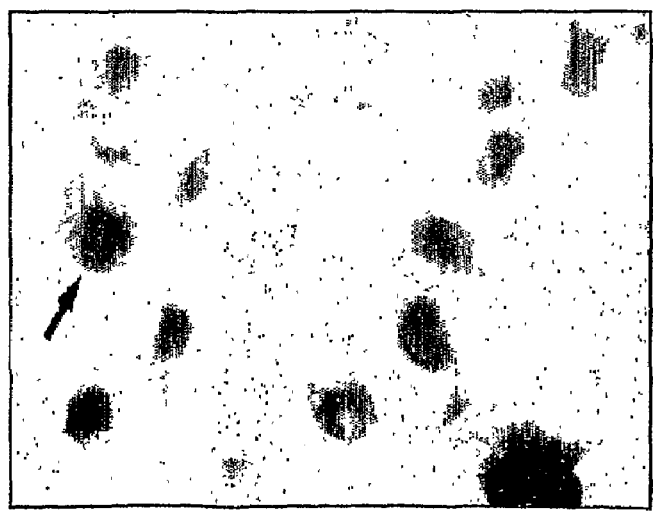
FIG. 3B—Refers to rat D, treated for 7 days, that exhibited a number of C. pneumoniae positive cells similar to rat A. However, in this case, the macrophages were detaching from the alveolar septa (arrow)—(H&E×1,000).
Figure 4A:
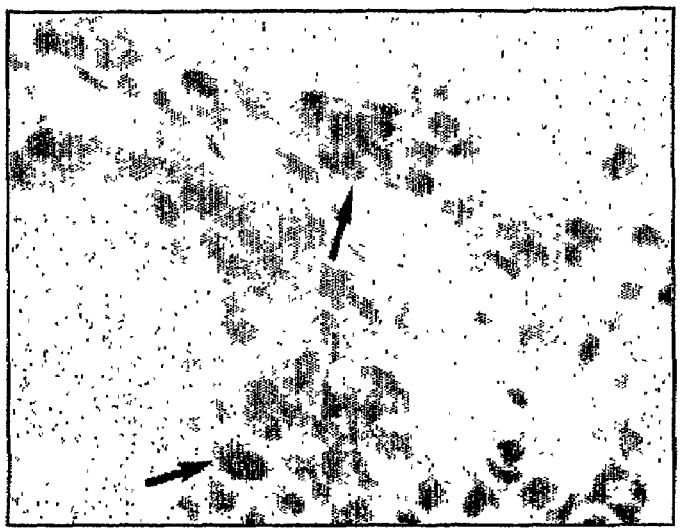
FIG. 4A—Refers to rat A, a non-treated animal. This rat exhibited bronchial epithelium with a proliferation of cells infected by M. pulmonis (in brown—arrows). M. pulmonis was also found in the interstitium of the alveolar septa (Immunoperoxidase—IPX—against M. pulmonis)—×1, 000)
Figure 4B:
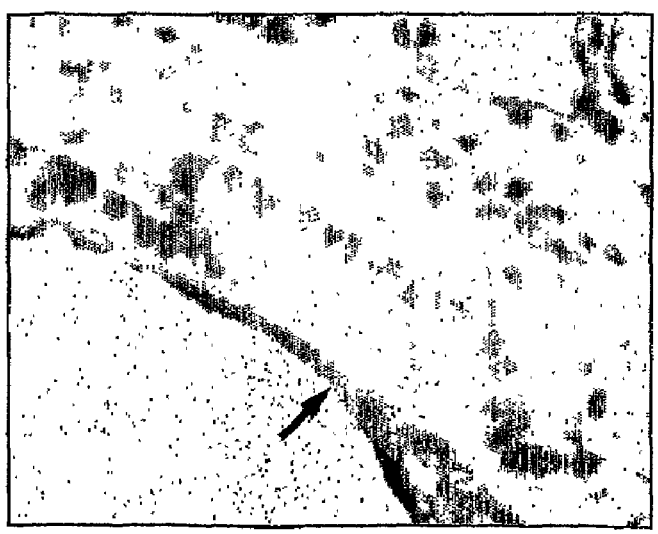
FIG. 4B—Refers to rat D (treated for 7 days) showing a layer of M. pulmonis (arrow) detaching from the bronchial epithelial surface, and the absence of M. pulmonis from the interstitium (Immunoperoxidase—against M. pulmonis—× 1,000)
Figure 5A:
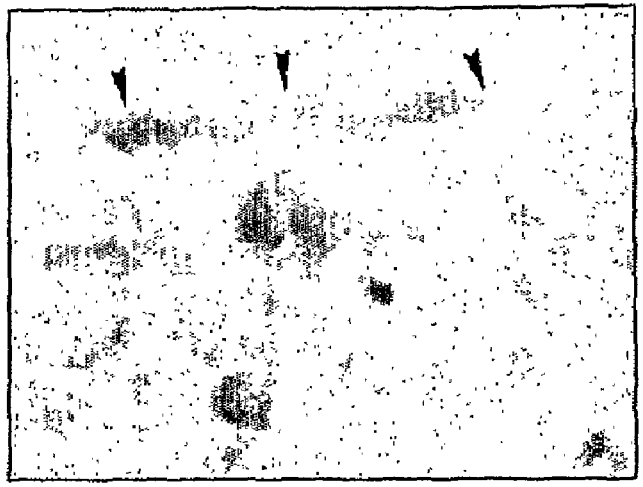
FIG. 5A—Refers to rat A (non-treated animal). It shows a large quantity of M. pulmonis (in brown) on the pleural surface (arrowheads), in the interstitium, and on the alveolar surface, in a diffuse and granular shape (Immunoperoxidase—against M. pulmonis—×1,000).
Figure 5B:
FIG. 5B—Refers to rat D, (treated for 7 days) presenting clearly defined M. pulmonis antigens on the alveolar surface; these are more compact and practically absent from the interstitium (immunoperoxidase—against M. pulmonis—× 1,000).
Figure 6A:
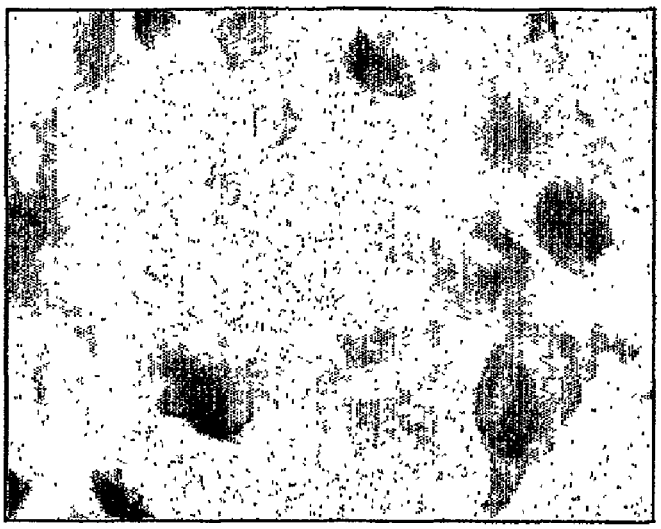
FIGS. 6A and 6B—Show aspects similar to FIGS. 5A and 5B, but depict a more internal region of the lung.
Figure 6B:
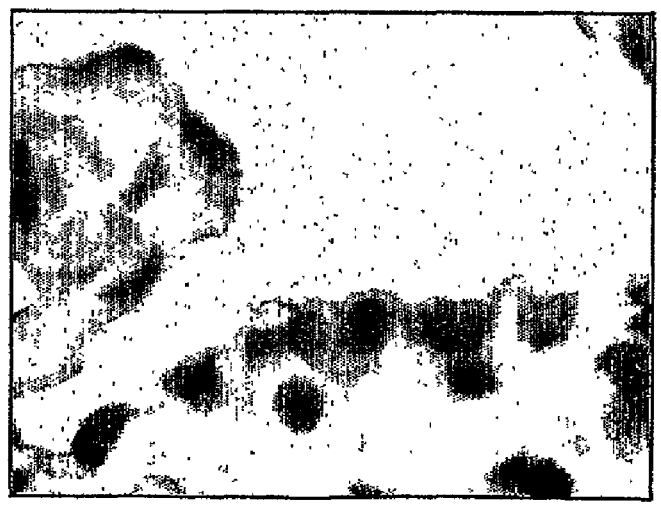
Figure 7A:
FIGS. 7A and 7B—Demonstrate the same differences described in the legends to FIGS. 5A and 5B, respectively, but in a 3D view obtained using confocal laser microscopy. M. pulmonis antigens were labeled with fluorescence and are shown in green.
Figure 7B:

Autopsy material from three patients who died of myocardial infarction had previously been analyzed for the presence of Chlamydia pneumoniae, and chlamydia were demonstrated in ruptured thrombosed coronary arteries (Higuchi et al., "Great amount of C. pneumoniae in ruptured plaque vessel segments at autopsy. A comparative study of stable plaques," *Arg. Bras. Cardiol.,* 74:149–151). A more detailed analysis of the autopsy material demonstrated that another microorganism was present in the unstable segments in the intima in association with the C. pneumoniae bodies. The electron microscopic characteristics that allowed the identification of these microorganisms as Mycoplasma pneumoniae included their rounded structures which contain a granulous chromatin-like material enveloped by a cytoplasmic membrane, in the absence of an external, cell wall. M. pneumoniae were adhered to the endothelial surface of the vasa vasorum (FIG. 1A) or were in the cytoplasm of cells also infected with C. pneumoniae. The mycoplasmas were present in blood monocytes and macrophages (FIG. 1B) or in the interstitium. Large numbers of these microorganisms were present inside the atheroma together with C. pneumoniae and were associated with several membrane components possibly corresponding to degenerated bacteria (FIG. 1C). Mycoplasma were also found in large cylindrical or elliptical forms in the extracellular matrix (FIG. 1D). These results were confirmed by in situ hybridization with a M. pneumoniae-specific probe from Enzo Diagnostics (New York, N.Y. USA). This technique, described in (Sambiase et al., "CMV and transplant-related coronary atherosclerosis: an immunohistochemical, in situ hybridization and polymerase chain reaction in situ study," *Modern Pathology* 13:173–179 (2000)), revealed a larger number of mycoplasmas mainly in unstable plaque segments throughout the fatty material or in the necrotic core (FIGS. 1E and 1F).

These findings demonstrate that i), the close association between chlamydia and mycoplasma seems to favor the proliferation of both microbes; ii) the development of atherosclerosis is linked to the presence of mycoplasmas; and iii) chagasic patients may possess a protective factor against infection by mycoplasmas. These experiments were reported in Higuchi et al., "Detection of Mycoplasma pneumoniae and Chlamydia pneumoniae in ruptured atherosclerotic plaques," *Braz. J. Med. Biol. Res.* 33:1023–1026 (2000), published after the priority date of this application.

EXAMPLE 2

Treatment of Mycoplasma-Infected Rats with Trans-Sialidase *T. Cruzi*

Both catalytic portion-recombinant form (TSC) and the complete native TS form (TSN) of *T. cruzi* were used to treat the infection caused by Mycoplasma pulmonis in association with Chlamydia pneumoniae afflicting most of the rats from the animal house of the São Paulo University School of Medicine. This supply system provides animals to many research laboratories at the São Paulo University School of Medicine and its Hospital.

Clinical Symptoms: The rats showed weight loss, conjunctivitis, otitis, slow movements, and increased transaminase levels. Animals with more severe clinical symptoms were usually separated for sacrifice, as they were unsuitable for use in experiments. An extensive battery of techniques for infection diagnosis was unable to detect any causative microorganism. By histological examination of various organs, together with immunohistochemical techniques using a monoclonal antibody against Chlamydia pneumoniae (from Dako Corporation, Calif., USA) and a polyclonal serum against Mycoplasma pulmonis (obtained by Prof. Jorge Timenetski from the Laboratory of Mycoplasmas, Biological Sciences Institute, São Paulo University) and electron microscopic analysis, it was possible to show that the alterations in the different organs were the result of a double infection by M. pulmonis and C. pneumoniae.

Experimental protocols: Nine adult rats (seven males and two females) weighing 285±36 g, presenting conjunctivitis and slow movements were studied. One animal, rat H, exhibited severe otitis that caused a deviation of its head to the right, and a tendency to move to the right. One of the female rats, rat F, showed severe weight loss.

Group A—Two control animals were killed without injecting any substance; another rat was killed on the seventh day, after receiving inactivated TSC substance for 5 consecutive days. There was no difference between this latter rat and the first two. These three animals were used as control animals exhibiting the usual pattern of the disease.

Group B—Five animals each received TSN (complete active native TS substance) every two days, employing a dose of 0.5 mL/animal, and were killed after seven, nine and twelve days of treatment. Another rat, rat D, received TSC (active TS substance catalytic portion, produced from a cloned bacteria) at a dose of 140 μg/day for five consecutive days, and was killed after seven days. Results:

Group A—Non-treated rats and rats treated with the inactivated TS substance.

The clinical symptoms are described above. The diagnosis of M. pulmonis and C. pneumoniae was performed by transmission electron microscopy, confocal laser microscopy and immunohistochemistry.

Lung was the most frequently injured organ. All rats presented histopathological signs of chronic tracheobronchitis, with different intensities of multi-focal, interstitial pneumonitis (FIG. 2A). A lympho-histiocytic infiltrate was present in the alveolar septa with many vacuolated macrophages in the interstitium and in the alveolar lumen (FIG. 3A). The tracheo-bronchial epithelium showed proliferation of the epithelial lining cells which were highly infected by M. pulmonis on their surface. The mycoplasmas were present both strongly attached to the epithelial cells, forming an irregular surface that stretched between adjacent cells, and in the cytoplasm of the lining cells (FIG. 4A). A large amount of M. pulmonis was present in the form of thin, delicate granules covering large areas of the pleural or subpleural areas (FIG. 5A), and also lining the alveolar surfaces, in macrophages or in the interstitial spaces (FIG. 6A). Both confocal (FIG. 7A) and electron microscopy (FIG. 8A) emphasized the irregular shape of the mycoplasmas, which extensively covered the alveolar surface and expanded into the alveolar septum.

The investigation on C. pneumoniae at the electron microscopy confirmed the presence of several elementary bodies of C. pneumoniae in the macrophages (FIG. 9A) and plasma cells. The immunohistochemistry revealed great amount of C. pneumoniae in the alveoli (FIGS. 10A and 11A).

There was a positive relationship between the amount of M. pulmonis and that of C. pneumoniae.

Examination of the heart revealed the occasional presence of chronic myocarditis and chronic valvulitis by a mononuclear cell infiltrate due to C. pneumoniae. In the liver, the presence of severe hydropic degeneration, steatosis, and interstitial inflammatory cells was noted. Severe otitis caused by M. pulmonis was noted in the ears.

Group B—Treated rats:

Clinical symptoms: There was a clear improvement in symptoms. The animals became more agile and the quantity of ether required to anesthetize them increased. Greater difficulty was found in restraining the animals than at the beginning of the experiment. The animal with otitis showed less loss of equilibrium and less head tilting. The female rat that lost weight became more agile and gained weight. The histological examination revealed that this female was infected with a large number of C. pneumoniae.

To analyze the effect of TS administration, the study mainly analyzed pulmonary alterations. Electron microscopy and confocal laser microscopy provided qualitative data, while the immunohistochemistry performed using the previously described antibodies, anti-M. pulmonis and anti-C. pneumoniae antibodies, provided quantitative data. The average number of cells positive for C. pneumoniae/400× field of lung tissue was obtained, and the percent area positive for M. pulmonis was obtained using an image analysis system (Leica Quantimet 500). The lack of a typical morphology for M. pulmonis did not permit quantification of their number.

Upon examination of the lung, histological sections showed that after 7 days of treatment the treated animals presented resolving pneumonitis (FIG. 2B). There was a great reduction of M. pulmonis in the alveolar lumen. In the respiratory epithelium, the mycoplasma were detaching from the septum to the lumen, with a clear decrease in the number of adhesion points (FIG. 3B).

At the respiratory epithelium, M. pulmonis was only found on the surface of epithelial cell, but not in their cytoplasm or between them, as shown by immunohistochemistry (FIG. 4B). The mycoplasmas on the alveolar and pleural surfaces had better defined limits (FIG. 5B). The FIG. 6B shows in closer view that the mycoplasma are still not into the cytoplasm of the cells. The morphology of M. pulmonis also changed, as visualized by confocal laser microscopy in 3D view; they were seen without the dendritic extensions that were visually seen in the non treated animals, the change seen by confocal microscopy: smaller micoorganisms and in lower amount (FIG. 8B). The C. pneumoniae by immunohistochemistry were present in macrophages with stronger staining and more homogeneous, than in the non-treated group, possibly suggesting peribronchial lymphoid nodes (FIG. 10B). There was a change in the morphological aspect of positive cells for C. pneumoniae in the alveoli (FIG. 11B). Although we did not have found decrease in the number of positive cells for C. pneumoniae after one week of treatment by immunohistochemistry, degenerated C. pneumoniae were detected by electron microscopy (FIG. 9B).

Figure 12A:
FIGS. 12A and 12B—Respectively show a panoramic (×100) and a higher magnification view (×1000) of rat G, after 12 days of treatment, revealing large areas from which M. pulmonis antigens are completely absent. However, the reactivity of the bronchial epithelium and the interstitial inflammation still present suggest that the lung was previously severely injured. (Immunoperoxidase against M. pulmonis).
Figure 12B:
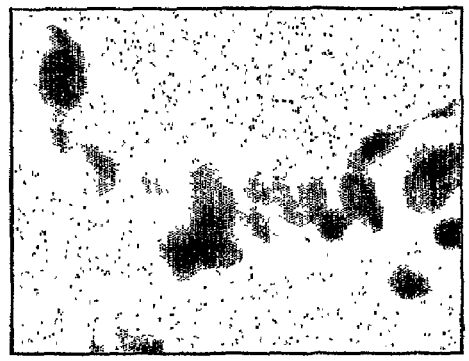
Figure 13A:
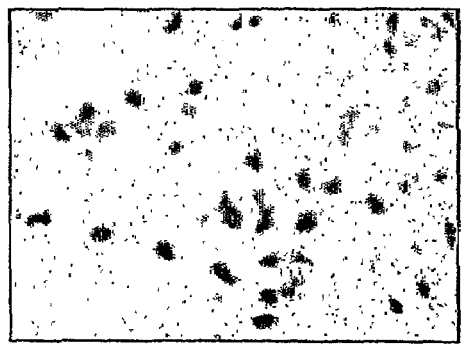
FIGS. 13A and 13B—Show resolving pneumonitis in rat G (12 days of treatment). C. pneumoniae antigens are almost absent both at moderate magnification (×250) and at high magnification (×1,000), which reveals vacuolated histiocytes free of C. pneumoniae antigens (immunoperoxidase against C. pneumoniae).
Figure 13B:
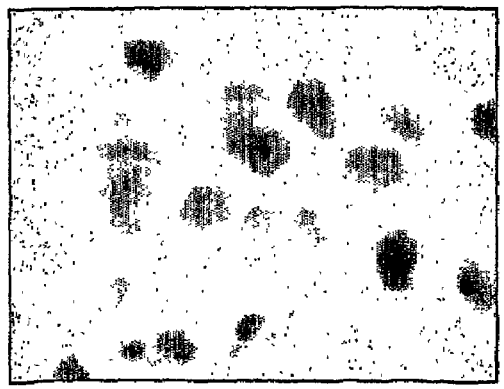

After 9–12 days of treatment, M. pulmonis were almost absent from alveoli (FIGS. 12A and 12B); in only one animal, we observed scarce positive foci on the surface of large bronchi. The reduction performed in an Image Analysis System showed reduction in the mean percentage area positive for M. pulmonis of C. pneumoniae positive cells was seen, and electron microscopy showed degenerative alterations after 12 days of treatment there was a decrease in the mean number of C. pneumoniae positive cells in the alveoli (FIGS. 13A and 13B). The positive cells were still present in the peribronchial lymphoid nodes, however restricted in the plasma cells, and not in the macrophages as were seen in the non-treated animals.

This situation is compatible with regression of the infection caused by C. pneumoniae. When other organs were examined, a clear regression of the histological alterations in general was observed. The kidney exhibited proliferative glomerulitis possibly due to the release of large quantities of circulating immune complexes. In the heart, myocarditis varied from absent to severe affliction, which made a comparative analysis of the results difficult.

Conclusions: The administration of trans-sialidase in rats infected with M. pulmonis and C. pneumoniae probably prevented the mycoplasma adhesion, leading to their detachment from the host cells, and characterized by their progressive disappearance from the lung tissue of the animals analyzed. The disappearance of the mycoplasmas probably leads to the loss of the synergistic mechanism of proliferation of C. pneumoniae, manifested in the decrease in number of C. pneumoniae positive cells and the degenerative aspect of the bacteria detected.

EXAMPLE 3

Comparison of Effectiveness of Trans-Sialidase Versus Neuraminidase

Generally, the sialidases irreversibly catalyse the transfer of sialic acid from glycoconjugates to water, in a reaction recognized as hydrolysis. However, the sialidases may also transfer sialic acid between galactose molecules, and can catalyze an reversible reaction denominated trans-sialation or more generically, trans-glycosylation.

The efficiency of the transferase activity versus hydrolysis depends on the concentration of acceptors containing free β-galactose. The *T. cruzi* trans-sialidase "TS" differs from the other sialidases because the acceptor concentration necessary for trans-glycosylation is much lower. Also, TS has a much lower catalytic efficiency in promoting hydrolysis, not depending on the acceptor concentration. This patent thus aims to investigate whether the removal of sialic acid or trans-sialation might provide a protective effect against mycoplasmas.

Using mycoplasma-infected rats, we tested the effect of bacterial sialidases that exhibit neuraminidase activity and very little trans-sialidase activity. Literature data show that mycoplasmas are sensitive to neuraminidase treatment and to pronase and other chemical agents, in vitro. The bacterial sialidases exhibit a lower specificity than the *T. cruzi* TS which acts only on sialic acid linked terminally by α2,3 linkages. In contrast, the bacterial sialidases hydrolyze bonds with terminal linkages α2,3; α2,6; α2,8, branched linkages, and glycoconjugates containing substitutions in the de β-galactosyl and adjacent residues, such as those found in the Lewis antigens, which are important factors in the linkage of adhesion molecules of the immune system. See, Vandekerckhove et al., "Substrate specificity of the *Trypanosoma cruzi* trans-sialidase" Glycobiology 2(6):541–8, 1992.

Experiments in Rats Using Neuraminidase:

A group of rats with clinical symptoms similar to those of the rats described in the previous experiments was submitted

|   | Initial weight | Final weight | % M. pulmonis area in the lung | No. C. pneumoniae +cells/400x field | Killed time | Substance injected | Time of administration |
|---|---|---|---|---|---|---|---|
| | | | Group A - Non-treated animals | | | | |
| A | 280 g | 280 g | 30.00 | 41.87 | 0 | nothing | — |
| B | 310 g | 310 g | 7.60 | 5.00 | 0 | nothing | — |
| C | 260 g | 270 g | 11.00 | 3.3 | 7 days | Inactivated | 5 consecutive days |
| | | | Group B - Treated animals | | | | |
| D | 290 g | 320 g | 13.78 | 43.4 | 7 days | Catalytic TS | 5 consecutive days |
| E | 356 g | 354 g | 0.90 | 1.6 | 5 days | Native TS | 2 alternated days |
| I | 278 g | 272 g | 4.52 | 18.5 | 7 days | Native TS | 3 alternated days |
| F | 232 g | 250 g | 7.80 | 45.0 | 9 days | Native TS | 4 alternated days |
| G | 303 g | 335 g | 0.30 | 2.5 | 12 days | Native TS | 5 alternated days |
| H | 258 g | 255 g | 2.80 | 16.6 | 12 days | Native TS | 5 alternated days | to treatment with sialidases/neuraminidase. This experiment was performed to verify whether these enzymes were effective in combating the diseases caused by mycoplasmas or by their association other infectious agents.

As there are many different bacterial sialidases, the present experiment was performed using two types of neuraminidase of different specificities. Four rats with a mean weight of 350 g were used. Rat #1 was treated for 5 consecutive days with *Vibrio cholerae* neuraminidase**. Rat #2 was treated for 5 consecutive days with *Clostridium perfringes* neuraminidase**. Rat #3 was treated for 5 consecutive days with the catalytic form of recombinant *T. cruzi* TS of (TSC). Finally, rat #4 received no treatment and was used as a control. All animals were sacrificed after 7 days.

Techniques:

The drug administration protocols for the first 3 rats were identical. To detect the amount of bacteria after treatment, we used the immunohistochemical technique already described in the first part of the present experiment.

Dosages:

Rat #1 received *Vibrio cholerae* from Roche Diagnostics, via daily intraperitoneal injection of 68 ul of the substance diluted in 432 μl of physiological saline.

In rat #2.—1.6 ul of *Clostridium perfringes* from Biolabs (catalog: #728S), diluted in 498.4 μl of physiological saline, was injected.

In rat #3.33 μl of the same TSC used in the first experiment, diluted in 500 μl of physiological saline, were used.

Rat #4, received no infection.

The amount of injected enzyme in each animal was estimated using an enzymatic assay employing a fluorescent substrate (4-methyl-umbelliferil-N-acetyl-neuramic acid), provided in the table below:

| Comparative data on Enzymatic activity: | | |
| --- | --- | --- |
| Enzyme Source | Dose (μl) | Enzymatic activity* |
| *Vibrio Cholerae*** neuraminidase | 68 | 0.0160 |
| *Clostridium Perfringes*** neuraminidase | 1.6 | 1.280 |
| TSC | 33 | 1.000 |

*Enzymatic activity corresponds to the amount of picomoles of methyl-1-umbeliferil-n-acetyl-neuraminic acid hydrolyzed in 1 minute at 37° C.
**from Roche Diagnostics.
***from New England Biolabs.

Results:

The results obtained are provided in the table below.

TABLE

| Neuraminidase experiment | | | | |
| --- | --- | --- | --- | --- |
| Rat | % area containing *M. pulmonis* in the lung | Number of *C. pneumoniae* positive Cells/ 400x field | Time until Sacrifice | Substance Injected | Duration of treatment |
| #1 | 15.7 | 9.3 | 7 days | *Vibrio Cholerae Neuraminidase** | 5 consecutive days |
| #2 | 13.1 | 5.0 | 7 days | *Clostridium Perfringes Neuraminidase*** | 5 consecutive days |
| #3 | 17.9 | 14.6 | 7 days | TSC | 5 consecutive days |
| #4 | 23.3 | 17.3 | 7 days | No treatment | — |

Analysis of the lung by immunohistochemistry demonstrated that the three treated rats exhibited M. pneumoniae antigens concentrated on the surface of bronchial epithelium, and not more in the interstitium of the alveolar septum, as usually seen in the non-treated rat (rat #4). Chlamydia pneumoniae antigens were seen in the macrophages. However, in the treated rats, the antigen distribution was homogeneous through the cytoplasm, possibly reflecting degraded bacteria. In the non-treated control rat, C. pneumoniae antigens were present in the form of granules.

Relevant alterations:

Rat #2 that received *Clostridium perfringes* neuraminidase presented an intense and diffuse pneumonia characterized by neutrophils with abscesses.

Conclusions:

This experiment showed that bacterial neuraminidases also remove mycoplasmas from the host cells. However, other adverse effects may occur. The severe pneumonia that rat #2 presented has not been seen previously in our experiments. The bacterial sialidases used in the present experiment are less specific in action, and may influence the immunological system of the host animal, favoring the proliferation of other bacteria or viruses. The trans-sialidase may be less dangerous because collateral effects were absent despite the greater amount of TS injected.

EXAMPLE 4

Effects of Trans-Sialidase on Human Cancer Cells in Culture

The following is data substantiating the discovery that mycoplasmas are present in cancer cells and may affect the natural biological process of cell death (apoptosis), transforming cells into permanently differentiated cells, thus playing a fundamental role in the pathogenesis of malignant neoplasia.

Figure 18:
FIG. 18—Electron microscopy revealing interlaced, irregular, filiform prolongations of the neoplasic cells that, together with information from other techniques, allowed identification as mycoplasmas. (Original magnification—2,000×).
Figure 19:
FIG. 19—Electron micrograph of a neoplasic cell from ovarian adenocarcinoma. The presence of a second membrane under the plasma membrane is compatible with the idea that the external prolongations are mycoplasmas intimately adhered to the neoplasic cell. (Original magnification—10,000×).
Figure 20:
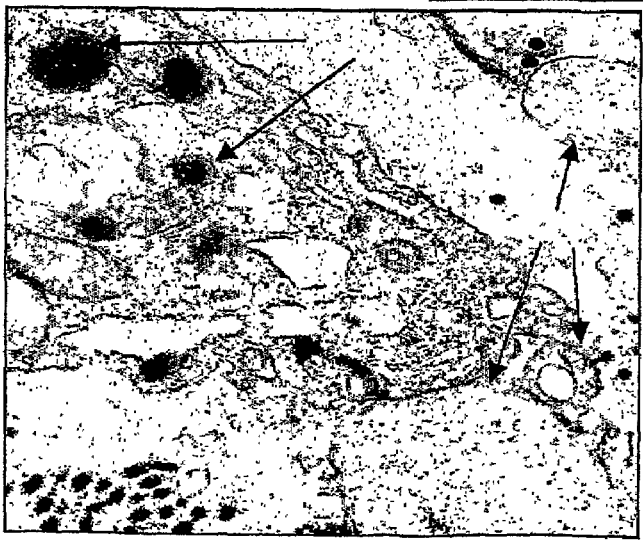
FIG. 20—Electron microscopic view showing a neoplasic cell from an ovarian adenocarcinoma presenting many C. pneumoniae granules in the cytoplasm (arrows at the top left) and mycoplasmas in the extracellular space, adhering to the surface of the neoplasic cell (arrows at right bottom). (Original magnification 7,200×).

In recent studies developed in the Laboratory of Pathology of the Heart Institute of the Clinical Hospital of the São Paulo University School of Medicine, we demonstrated that different malignant neoplasias such as adenocarcinomas of the bladder, lung, stomach and large intestine, as well as mesotheliomas, are severely infected with mycoplasmas in association with Chlamydia pneumoniae. This conclusion was based on data from in situ hybridization (FIG. 14), imunohistochemistry (FIG. 15), confocal laser microscopy (FIG. 16) and electron microscopy (FIGS. 18, 19 and 20). The data agree with recent in vitro demonstrations that mycoplasmas may induce malignant transformation in rat cells (Feng Shaw-Huey, et al.,"Mycoplasma infections prevent apoptosis and induce malignant transformation of interleuckin-3-dependent 32 D hematopoietic cells," *Mol Cel Biol* 19(12): 7995–8—2, (1999)). It has already been demonstrated that malignant neoplasia is frequently associated with higher levels of sialic acid in the serum of these patients (Ros-Bullon, et al., "Serum sialic acid in malignant melanoma patients: na ROC curve analysis," *Anticancer Res* 19(4C): 3619–22 (1999); Berbec et al., "Total serum sialic acid concentration as a supporting marker of malignancy in ovarian neoplasia," *Eur J Gynaecol Oncol* 20(5–6): 389–92 (1999)).

Neoplasic cells from the ascites fluid of two patients with ovarian adenocarcinoma, and from a patient with malignant mesothelioma of the peritoneum, were found to exhibit intensely positive staining for M. pneumoniae and Mycoplasma pulmonis antigens using the immunoperoxidase technique. The neoplasic cells from each of the respective ascites fluids were cultivated in two plates containing 8 wells. After 3 days, native trans-sialidase (TSN) was added to the culture medium in half the wells. One plate was examined 3 days and the other 5 days after TSN addition. The cell culture in each well was stained using a double immunofluorescent staining technique, employing the following combinations: nuclear stain (Cy-5)+M. pulmonis antigens (fluorescein); nuclear (Cy-5)+M. pneumoniae antigens (fluorescein); and nuclear stain (Cy-5)+apoptotic nuclei detected by the TUNEL method (fluorescein).

Figure 21:
FIG. 21—Double staining immunofluorescence technique demonstrating M. pulmonis antigens (stained in green by fluorescein, revealing the external prolongations), and nuclei in red (Cy-5) in a clump of neoplasic cells from an ovarian adenocarcinoma. The yellow regions represent the superposition of the green and red labeled areas (Original magnification—100×).
Figure 22:
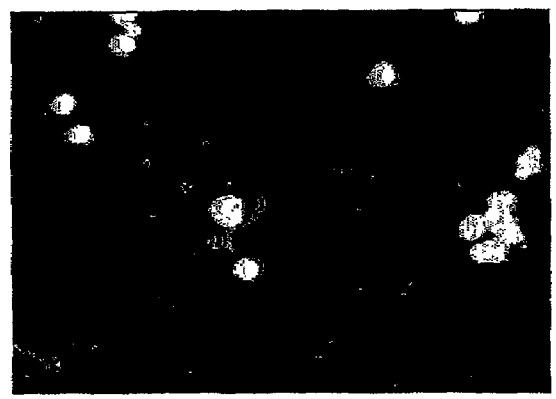
FIG. 22—Ovarian adenocarcinoma culture treated with TSN for 5 days. The decrease in amount of M. pulmonis antigens is remarkable (Confocal laser microscopy—Original magnification—100×).
Figure 23:
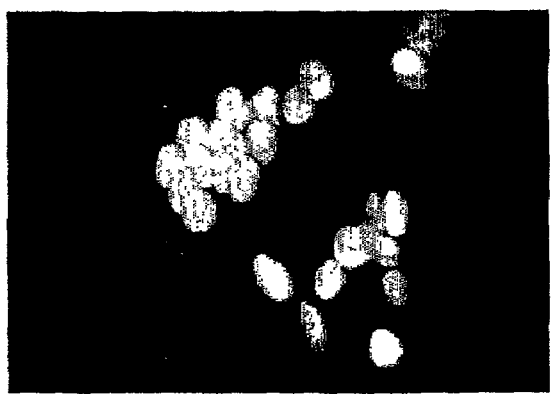
FIG. 23—Clump of neoplasic cells in culture. The TUNEL technique reveals only a single cell in apoptosis (part of the nuclei in yellow)—(Confocal laser microscopy—original magnification—100×).
Figure 24:
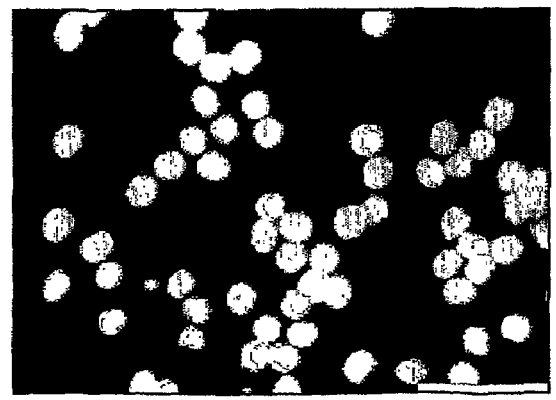
FIG. 24—Ovarian adenocarcinoma cell culture to which TS was added. The cells lost the adherence and entered apoptosis as detected by the TUNEL technique (positive results are nuclei in yellow), after 3 days of TS administration (Confocal laser microscopy—Original magnification—100×).

The results are depicted in FIGS. 21, 22, 23 and 24. The culture cells that did not receive TSN grew, maintaining initial cohesion, forming a clump of neoplasic cells (FIGS. 21 and 23). However, the cultures receiving TSN exhibited cells that lost adherence each other, taking on the appearance of a cell monolayer (FIGS. 22 and 24). The TUNEL technique demonstrated that the samples receiving TSN contained a large number of apoptotic cells already after 3 days of treatment, that increased after 5 days (FIG. 24). In contrast, the cultures that did not receive TSN showed very few cells in apoptosis (FIG. 23). The double staining immunofluorescence technique, using anti-mycoplasma antigens and anti-nuclei, showed that, in contrast to the control cultures (FIG. 21), M. pulmonis was no longer detectable in the peripheral cytoplasm on the cell surface after 3 days of treatment with TSN (FIG. 22). After 5 days of treatment, there was a decrease in the amount of M. pneumoniae antigens.

In summary, a decrease in the anti-M. pulmonis and anti-M. pneumoniae antigen stain was found to occur simultaneously with an increase in the number of neoplasic cells that had entered apoptosis, in the wells receiving TSN. This is consistent with the conclusion that the removal of mycoplasmas from neoplasic cells induces apoptosis in these cells.

EXAMPLE 5

Effect of Trans-Sialidase on Human Cancers In Vivo

A Phase I study to evaluate the use of trans-sialidase in the treatment of solid malignant neoplasias was performed at the Heart Institute of São Paulo Clinical Hospital. This study, approved by the Ethics Committee of the Institute, had the objective of evaluating the toxicity of *T. cruzi* trans-sialidase, and its effects in the treatment of neoplasias positive for mycoplasmas (detected by immunohistochemistry).

Two patients in the terminal phase of their disease (stage IV) and unresponsive to conventional therapies (radiotherapy and chemotherapy) were submitted to this new treatment protocol.

Cytotoxic effects were not seen after two weeks of treatment and, a significant reduction in the tumoral mass was detected after three weeks by clinical palpation and tomographic analysis.

Patient No. 1:

The first patient, a 64 year old, female, had been diagnosed with ovarian adenocarcinoma in 1990, when the tumor was resected. She received chemotherapy (2 cycles) interrupted as a result of toxicity. In July 1997, she presented a recurrence of the cancer, and was treated by chemotherapy with Carboplatine. In February 1998, a second recurrence was found, and she was treated with radiotherapy. In March 1999, after a further recurrence of the tumor, chemotherapy with 3 cycles of Taxol was performed. This treatment was also interrupted by cytotoxicity. Intestinal hemorrhage by tumoral rectal infiltration appeared. Subsequently, laparotomy revealed a recurrence of the tumor that was considered inoperable and a colostomy was performed.

The patient presented for the protocol with a palpable abdominal mass and a tumoral mass in the rectum revealed by the tomography. The patient exhibited cachexia, weighed 44 kg, with a height of 1.53 m.

The protocol used on this patient is as follows. The patient was administered 50 ml of native trans-sialidase ("TSN"), intraperitoneally, corresponding to 140 U activity, on alternate days, during a period of 14 days.

Enzyme activity—1 U corresponds to 30,000 cpm at 37° C., during 30 minutes.

The patient experienced abdominal pain on the third day of drug administration which was controlled with Tramadol Chlorhydrate 50 mg. On the 9th day, the patient presented vomiting, interpreted as adherence or carcinomatosis by the surgical medical team. This episode was resolved without surgical intervention. On the 22nd day, 5 days after the end of the first cycle of treatment, she presented fever (37.8° C.) and leucopenia (1.000 leucocytes/mm$^3$) in the blood examination. She received Rocefin 1.0 g every 12 h and subcutaneous granuloquine, 300 µg/day.

On the 23rd day, with mycoplasmas confirmed in the bone marrow, Erythromycin 500 mg/day was given for a further 20 days. Clinical improvement and normalization of blood leucocytes was seen after two days. Considering the important clinical improvement and reduction in abdominal mass, a second session of TSN was administered under the same conditions. The patient did not show toxicity.

In summary, the patient demonstrated improvement in general clinical status. Tomography detected a reduction in the tumoral mass. The rectal infiltration was difficult to evaluate by tomography and by magnetic resonance imaging (MRI).

Patient No. 2:

The second patient was a 69 year old female who had, within the previous year, submitted to a laparotomy to diagnose the cause of ascites. A diagnosis of Malignant Mesothelioma affecting the entire peritoneum was established. Shortly thereafter, the patient was treated with chemotherapy but showed no response. The tumor continued to grow quickly.

The patient soon began the protocol. She received recombinant catalytic fragment trans-sialidase (TSC) 4.0 mg/day, during 14 consecutive days. The corresponding activity was 3.4×10$^7$ U/day. She presented with fever at the end of the second week of treatment that was controlled with Cypro 1.0 g/day. The number of blood leucocytes was unaltered. Tomography showed a reduction in the tumor, and the patient showed improvement in the clinical state.

Conclusion:

The results obtained with these two patients treated with trans-sialidase, both in the native state or as the recombinant form of the catalytic portion, show that TS is effective as a drug in the treatment of neoplasia, removing mycoplasmas from the neoplasic cells, probably leading to their apoptosis.

Various publications are cited herein, the contents of which are hereby incorporated by reference in their entireties.

The invention claimed is:

1. A method for treating undesirable cell proliferation associated with mycoplasma infection in a subject comprising administering to the subject an effective amount of an agent that inhibits sialic acid-mediated attachment of mycoplasma to cells of the subject, wherein the agent is selected from the group consisting of an enzyme having trans-sialidase activity, and an enzyme having neuraminidase activity, and a combination thereof.

2. The method of claim 1, wherein the enzyme is obtained from *Trypanosoma cruzi*.

3. The method of claim 2, wherein the enzyme has an amino acid sequence set forth in SEQ ID NO:2.

4. The method of claim 1, wherein the disorder is atherosclerosis.

5. The method of claim 1, wherein the disorder is malignancy.

* * * * *

SEQUENCE LISTING

<160> NUMBER OF SEQ ID NOS: 4

<210> SEQ ID NO 1
<211> LENGTH: 2010
<212> TYPE: DNA
<213> ORGANISM: Artificial Sequence
<220> FEATURE:
<223> OTHER INFORMATION: Variant of T. Cruzi trans-sialidase gene

<400> SEQUENCE: 1

```
atgggcagca gccatcatca tcatcatcac agcagcggcc tggtgccgcg cggcagccat     60
atggcacccg gatcgagccg agttgagctg tttaagcggc aaagctcgaa ggtgccattt    120
gaaaagggcg gcaaagtcac cgagcgggtt gtccactcgt tccgcctccc cgcccttgtt    180
aatgtggacg gggtgatggt tgccatcgcg gacgctcgct acgaaacatc caatgacaac    240
tccctcattg atacggtggc gaagtacagc gtggacgatg ggagacgtg ggagacccaa     300 attgccatca agaacagtcg tgcatcgtct gtttctcgtg tggtggatcc cacagtgatt    360
gtgaagggca acaagcttta cgtcctggtt ggaagctaca acagttcgag gagctactgg    420
acgtcgcatg gtgatgcgag agactgggat attctgcttg ccgttggtga ggtcacgaag    480
tccactgcgg gcggcaagat aactgcgagt atcaaatggg ggagccccgt gtcactgaag    540
gaatttttcc cggcggaaat ggaaggaatg cacacaaatc aatttcttgg cggtgcaggt    600
gttgccattg tggcgtccaa cgggaatctt gtgtaccctg tgcaggttac gaacaaaaag    660
aagcaagttt tttccaagat cttctactcg gaagacgagg gcaagacgtg gaagtttggg    720
gagggtagga gtgattttgg ctgctctgaa cctgtggccc ttgagtggga ggggaagctc    780
atcataaaca ctcgagttga ctatcgccgc cgtctggtgt acgagtccag tgacatgggg    840
aattcgtggg tggaggctgt cggcacgctc tcacgtgtgt ggggcccctc accaaaatcg    900
aaccagcccg gcagtcagag cagcttcact gccgtgacca tcgagggaat gcgtgttatg    960
ctcttcacac acccgctgaa ttttaaggga aggtggctgc gcgaccgact gaacctctgg   1020
ctgacggata accagcgcat ttataacgtt gggcaagtat ccattggtga tgaaaattcc   1080
gcctacagct ccgtcctgta caaggatgat aagctgtact gtttgcatga gatcaacagt   1140
aacgaggtgt acagccttgt ttttgcgcgc ctggttggcg agctacggat cattaaatca   1200
gtgctgcagt cctggaagaa ttgggacagc cacctgtcca gcatttgcac ccctgctgat   1260
ccagccgctt cgtcgtcaga gcgtggttgt ggtcccgctg tcaccacggt tggtcttgtt   1320
ggctttttgt cgcacagtgc caccaaaacc gaatgggagg atgcgtaccg ctgcgtcaac   1380
gcaagcacgg caaatgcgga gagggttccg aacggtttga agtttgcggg ggttggcgga   1440
ggggcgcttt ggccggtgag ccagcagggg cagaatcaac ggtatcactt tgcaaaccac   1500
gcgttcacgc tggtggcgtc ggtgacgatt cacgaggttc cgagcgtcgc gagtcctttg   1560
ctgggtgcga gcctggactc ttctggtggc aaaaaactcc tggggctctc gtacgacgag   1620
aagcaccagt ggcagccaat atacggatca acgccggtga cgccgaccgg atcgtgggag   1680
atgggtaaga ggtaccacgt ggttcttacg atggcgaata aaattggttc ggtgtacatt   1740
gatggagaac ctctggaggg ttcagggcag accgttgtgc cagacgggag gacgcctgac   1800
atctcccact tctacgttgg cgggtatgga aggagtgata tgccaaccat aagccacgtg   1860
acggtgaata atgttcttct ttacaaccgt cagctgaatg ccgaggagat caggaccttg   1920
ttcttgagcc aggacctgat tggcacggaa gcacacatgg gcagcagcag cggcagcagt   1980
```
gaaagaagta cgcccggatc cggctgctaa          2010

<210> SEQ ID NO 2
<211> LENGTH: 669
<212> TYPE: PRT
<213> ORGANISM: Artificial Sequence
<220> FEATURE:
<223> OTHER INFORMATION: Variant of T. Cruzi trans-sialidase protein

<400> SEQUENCE: 2

```
Met Gly Ser Ser His His His His His His Ser Ser Gly Leu Val Pro
1               5                   10                  15

Arg Gly Ser His Met Ala Pro Gly Ser Ser Arg Val Glu Leu Phe Lys
            20                  25                  30

Arg Gln Ser Ser Lys Val Pro Phe Glu Lys Gly Lys Val Thr Glu
        35                  40                  45

Arg Val Val His Ser Phe Arg Leu Pro Ala Leu Val Asn Val Asp Gly
    50                  55                  60

Val Met Val Ala Ile Ala Asp Ala Arg Tyr Glu Thr Ser Asn Asp Asn
65                  70                  75                  80

Ser Leu Ile Asp Thr Val Ala Lys Tyr Ser Val Asp Asp Gly Glu Thr
                85                  90                  95

Trp Glu Thr Gln Ile Ala Ile Lys Asn Ser Arg Ala Ser Ser Val Ser
            100                 105                 110

Arg Val Val Asp Pro Thr Val Ile Val Lys Gly Asn Lys Leu Tyr Val
        115                 120                 125

Leu Val Gly Ser Tyr Asn Ser Ser Arg Ser Tyr Trp Thr Ser His Gly
    130                 135                 140

Asp Ala Arg Asp Trp Asp Ile Leu Leu Ala Val Gly Glu Val Thr Lys
145                 150                 155                 160

Ser Thr Ala Gly Gly Lys Ile Thr Ala Ser Ile Lys Trp Gly Ser Pro
                165                 170                 175

Val Ser Leu Lys Glu Phe Phe Pro Ala Glu Met Glu Gly Met His Thr
            180                 185                 190

Asn Gln Phe Leu Gly Gly Ala Gly Val Ala Ile Val Ala Ser Asn Gly
        195                 200                 205

Asn Leu Val Tyr Pro Val Gln Val Thr Asn Lys Lys Gln Val Phe
    210                 215                 220

Ser Lys Ile Phe Tyr Ser Glu Asp Glu Gly Lys Thr Trp Lys Phe Gly
225                 230                 235                 240

Glu Gly Arg Ser Asp Phe Gly Cys Ser Glu Pro Val Ala Leu Glu Trp
                245                 250                 255

Glu Gly Lys Leu Ile Ile Asn Thr Arg Val Asp Tyr Arg Arg Arg Leu
            260                 265                 270

Val Tyr Glu Ser Ser Asp Met Gly Asn Ser Trp Val Glu Ala Val Gly
        275                 280                 285

Thr Leu Ser Arg Val Trp Gly Pro Ser Pro Lys Ser Asn Gln Pro Gly
    290                 295                 300

Ser Gln Ser Ser Phe Thr Ala Val Thr Ile Glu Gly Met Arg Val Met
305                 310                 315                 320

Leu Phe Thr His Pro Leu Asn Phe Lys Gly Arg Trp Leu Arg Asp Arg
                325                 330                 335

Leu Asn Leu Trp Leu Thr Asp Asn Gln Arg Ile Tyr Asn Val Gly Gln
            340                 345                 350
```

-continued

```
Val Ser Ile Gly Asp Glu Asn Ser Ala Tyr Ser Ser Val Leu Tyr Lys
        355                 360                 365
Asp Asp Lys Leu Tyr Cys Leu His Glu Ile Asn Ser Asn Glu Val Tyr
    370                 375                 380
Ser Leu Val Phe Ala Arg Leu Val Gly Glu Leu Arg Ile Ile Lys Ser
385                 390                 395                 400
Val Leu Gln Ser Trp Lys Asn Trp Asp Ser His Leu Ser Ser Ile Cys
                405                 410                 415
Thr Pro Ala Asp Pro Ala Ala Ser Ser Glu Arg Gly Cys Gly Pro
            420                 425                 430
Ala Val Thr Thr Val Gly Leu Val Gly Phe Leu Ser His Ser Ala Thr
            435                 440                 445
Lys Thr Glu Trp Glu Asp Ala Tyr Arg Cys Val Asn Ala Ser Thr Ala
            450                 455                 460
Asn Ala Glu Arg Val Pro Asn Gly Leu Lys Phe Ala Gly Val Gly Gly
465                 470                 475                 480
Gly Ala Leu Trp Pro Val Ser Gln Gln Gly Gln Asn Gln Arg Tyr His
                485                 490                 495
Phe Ala Asn His Ala Phe Thr Leu Val Ala Ser Val Thr Ile His Glu
                500                 505                 510
Val Pro Ser Val Ala Ser Pro Leu Leu Gly Ala Ser Leu Asp Ser Ser
            515                 520                 525
Gly Gly Lys Lys Leu Leu Gly Leu Ser Tyr Asp Glu Lys His Gln Trp
        530                 535                 540
Gln Pro Ile Tyr Gly Ser Thr Pro Val Thr Pro Thr Gly Ser Trp Glu
545                 550                 555                 560
Met Gly Lys Arg Tyr His Val Val Leu Thr Met Ala Asn Lys Ile Gly
                565                 570                 575
Ser Val Tyr Ile Asp Gly Glu Pro Leu Glu Gly Ser Gly Gln Thr Val
            580                 585                 590
Val Pro Asp Gly Arg Thr Pro Asp Ile Ser His Phe Tyr Val Gly Gly
            595                 600                 605
Tyr Gly Arg Ser Asp Met Pro Thr Ile Ser His Val Thr Val Asn Asn
        610                 615                 620
Val Leu Leu Tyr Asn Arg Gln Leu Asn Ala Glu Glu Ile Arg Thr Leu
625                 630                 635                 640
Phe Leu Ser Gln Asp Leu Ile Gly Thr Glu Ala His Met Gly Ser Ser
                645                 650                 655
Ser Gly Ser Ser Glu Arg Ser Thr Pro Gly Ser Gly Cys
            660                 665
```

```
<210> SEQ ID NO 3
<211> LENGTH: 28
<212> TYPE: DNA
<213> ORGANISM: Artificial Sequence
<220> FEATURE:
<223> OTHER INFORMATION: Trans-sialidase gene primer

<400> SEQUENCE: 3
ggaattccat atggcacccg gatcgagc                                      28

<210> SEQ ID NO 4
<211> LENGTH: 34
<212> TYPE: DNA
<213> ORGANISM: Artificial Sequence
<220> FEATURE:
<223> OTHER INFORMATION: Trans-sialidase gene primer
```

```
<400> SEQUENCE: 4
cggatccggg cgtacttctt tcactggtgc cggt                              34
```